United States Patent
Dhanoa

(10) Patent No.: US 8,618,116 B2
(45) Date of Patent: *Dec. 31, 2013

(54) DEUTERIUM-ENRICHED PYRIMIDINE COMPOUNDS AND DERIVATIVES

(76) Inventor: Daljit Singh Dhanoa, Del Mar, CA (US)

(*) Notice: Subject to any disclaimer, the term of this patent is extended or adjusted under 35 U.S.C. 154(b) by 358 days.

This patent is subject to a terminal disclaimer.

(21) Appl. No.: 12/804,970

(22) Filed: Aug. 3, 2010

(65) Prior Publication Data

US 2011/0028496 A1    Feb. 3, 2011

Related U.S. Application Data

(60) Provisional application No. 61/273,247, filed on Aug. 3, 2009.

(51) Int. Cl.
*C07D 495/04* (2006.01)
*A61K 31/519* (2006.01)
*A61P 9/12* (2006.01)
*A61P 25/28* (2006.01)

(52) U.S. Cl.
USPC .......... 514/260.1; 544/278

(58) Field of Classification Search
USPC .......... 544/278; 514/260.1
See application file for complete search history.

(56) References Cited

U.S. PATENT DOCUMENTS

| | | | |
|---|---|---|---|
| 6,221,335 B1* | 4/2001 | Foster | 424/1.81 |
| 6,440,710 B1* | 8/2002 | Keinan et al. | 435/148 |
| 6,603,008 B1* | 8/2003 | Ando et al. | 546/269.7 |
| 7,517,990 B2* | 4/2009 | Ito et al. | 546/184 |
| 2005/0222176 A1* | 10/2005 | Dhanoa et al. | 514/260.1 |
| 2007/0082929 A1* | 4/2007 | Gant et al. | 514/338 |
| 2007/0197695 A1* | 8/2007 | Potyen et al. | 524/110 |

OTHER PUBLICATIONS

Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982.*
Wolen, Journal of Clinical Pharmacology 1986; 26: 419-424.*
Browne, Journal of Clinical Pharmacology1998; 38: 213-220.*
Baillie, Pharmacology Rev.1981; 33: 81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol.1999; 39: 817-825.*
Honma et al., Drug Metab Dispos 15 (4): 551 (1987).*

* cited by examiner

Primary Examiner — Susanna Moore
(74) Attorney, Agent, or Firm — Karl Neidert

(57) ABSTRACT

The present invention is concerned with deuterium-enriched pyrimidine compounds of formula I, their derivatives and pharmaceutically acceptable salts and methods of use thereof

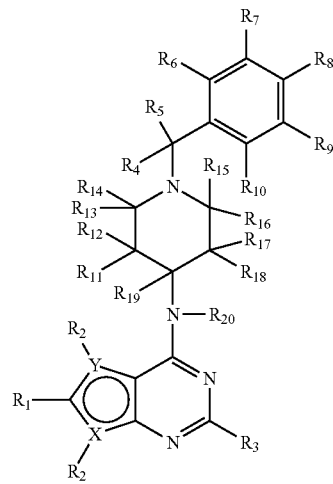

for the treatment of pulmonary arterial hypertension, pulmonary hypertension associated with chronic obstructive pulmonary disease (COPD), asthma, cystic fibrosis, hypertension, ischemic stroke, angina pectoris, congestive heart failure, arrhythmia, arterial fibrillation, Alzheimer's disease, cognition impairment, memory decline, and schizophrenia, and depression.

11 Claims, No Drawings

DEUTERIUM-ENRICHED PYRIMIDINE COMPOUNDS AND DERIVATIVES

CROSS-REFERENCE TO RELATED APPLICATIONS

The present application claims priority benefit under 35 U.S.C. article section 119 (e) of U.S. Provisional Patent Application Ser. No. U.S. 61/273,247 filed Aug. 3, 2009. The disclosure of this application is incorporated herein by reference.

SUMMARY OF THE INVENTION

This invention is concerned with pyrimidine compounds and their derivatives of the formula I and pharmaceutically acceptable salts thereof,

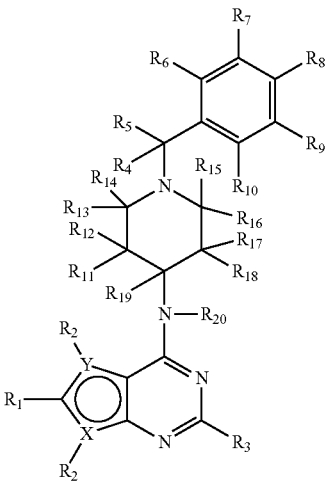

I wherein,
when X=S, Y is C or N; when Y is C, it is substituted with $R_2$;
when Y=S, X is C or N; when X is C, it is substituted with $R_2$;
$R_1$ is D (Deuterium), F, Cl;
$R_2$ is D, F, Cl;
$R_3$ is H, D;
$R_4$ and $R_5$ are D, H;
$R_6$, $R_7$, $R_8$, $R_9$ and $R_{10}$ are D, H, F, Cl, CN;
$R_{11}$, $R_{12}$, $R_{13}$, $R_{14}$, $R_{15}$, $R_{16}$, $R_{17}$, $R_{18}$, and $R_{19}$ are D, H;
$R_{20}$ is D, H;
and salts thereof.

BACKGROUND OF THE INVENTION

Neurotransmitter serotonin or 5-Hydroxytryptamine (5-HT) is abundantly distributed in the central nervous system, including hippocampus and frontal cortex. 5-HT receptors are a family of G-protein coupled receptors, characterized with 7-transmembrane helices and presently have fourteen known receptor subtypes, some of which exist as multiple splice variants [D. L. Murphy, A. M. Andrews, C. H. Wichems, Q. Li, M. Tohda and B. Greenberg, *J. Clin. Psychiatry*, 1998, 59 (suppl. 15), 4]. 5-HT influences a number of physiological functions and is implicated in a large number of central nervous system disorders and neurodegenerative diseases [W. E. Childers, Jr. and A. J. Robichaud, *Ann. Rep. Med. Chem.* 2005, 40, 17].

5-$HT_{2B}$ receptors are widely distributed in mammalian peripheral tissues including lung, heart, pancreas, spleen, prostate, liver, vascular and skeletal muscle, adipose tissue, intestine, ovary, uterus, testis, and in the central nervous system (CNS) including brain and cereberal cortex. 5-$HT_{2B}$ receptors are present in many vascular beds and have been localized to both vascular smooth muscle and vascular endothelial cells in humans. The receptor was characterized in the rat gastric (fundus) smooth muscle cells initially as the receptor responsible mediating serotonin-induced contraction in this tissue.

5-$HT_{2B}$ receptor antagonists have the potential to be selective for diseased pulmonary trachea, thymus, thyroid, salivary gland vasculature (i.e., vessels affected by hypoxic conditions) compared to normal pulmonary and systemic vessels. Due to this selectivity, 5-$HT_{2B}$ antagonists offer a possible therapeutic advantage over the available agents for the treatment of pulmonary arterial hypertension and related disease of the lung and vascular system.

Pulmonary hypertension (PH) is a progressive, debilitating and often fatal disease that results from an increase in pulmonary blood pressure associated with abnormal vascular proliferation. PH is estimated to affect 100,000 people worldwide. Current treatments include systemically administered intravenous and subcutaneous prostacyclin analogs and orally active endothelin receptor antagonists, which mainly cause pulmonary arterial dilation to relieve symptoms. There is only one approved orally active agent for PH available for patients, a non-specific endothelin A and B receptor antagonist which requires liver toxicity monitoring.

The novel compounds of formula I have 5-$HT_{2B}$ receptor antagonist activity and have applications as safer and effective therapeutic drugs for the treatment of pulmonary arterial hypertension, resistant hypertension, hypertension, congestive heart failure and erectile dysfunction, Alzheimer's disease, and age-related cognitive and memory dysfunction and cognitive and memory impairment associated with schizophrenia. These compounds may also have applications in the treatment of gastrointestinal disorders including irritable bowel syndrome, Crohn's disease, gastroesophageal reflux disease, emesis, nausea, vomiting, prokinesia, non-ulcer dyspepcia, anxiety, depression, pain, migraine, urinary incontinence, arterial fibrillation, arrhythmia, ischemic stroke, gastric emptying disorders, gastritis, gastrointestinal disorders, feeding disorders, obesity, anorexia, constipation, constipation, and respiratory depression.

DETAILED DESCRIPTION OF THE INVENTION

This invention is concerned with pyrimidine compounds and their derivatives of the formula I and pharmaceutically acceptable salts thereof,

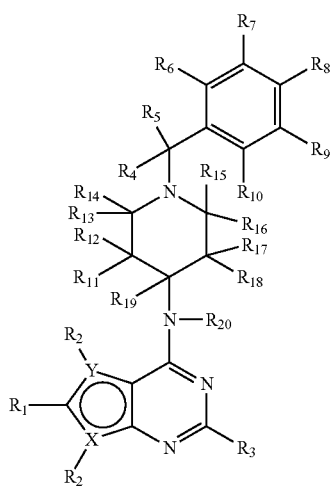

wherein,
when X=S, Y is C or N; when Y is C, it is substituted with $R_2$;
when Y=S, X is C or N; when X is C, it is substituted with $R_2$;
$R_1$ is D (Deuterium), H, F, Cl;
$R_2$ is D, H, F, Cl;
$R_3$ is H, D;
$R_4$ and $R_5$ are D, H;
$R_6$, $R_7$, $R_8$, $R_9$ and $R_{10}$ are D, H, F, Cl, CN;
$R_{11}$, $R_{12}$, $R_{13}$, $R_{14}$, $R_{15}$, $R_{16}$, $R_{17}$, $R_{18}$, and $R_{19}$ are D, H;
$R_{20}$ is D, H;
and salts thereof.

Pharmaceutically acceptable salts selected from the group consisting of hydrochloride, acetate, trifluoroacetate, mesylate, maleate, broselate, fumarate, maleic, malic, citrate, tartrate, sodium, potassium, calcium and magnesium salts.

The compounds of formula I have antagonist or agonist activity for serotonin receptor subtypes 2B (5-$HT_{2B}$ receptor), 5-$HT_{1A}$ and dopamine receptors, and these compounds and pharmaceutical salts thereof can accordingly be used for the treatment of diseases associated with these receptors, especially pulmonary arterial hypertension, pulmonary hypertension associated with chronic obstructive pulmonary disease (COPD), asthma, cystic fibrosis, hypertension, ischemic stroke, angina pectoris, congestive heart failure, arrhythmia, arterial fibrillation, Alzheimer's disease, cognition impairment, memory decline, and schizophrenia, and depression.

A preferred group of compounds of formula I are those in which,
when X=S, Y is C or N; when Y is C, it is substituted with $R_2$;
when Y=S, X is C or N; when X is C, it is substituted with $R_2$;
$R_1$ is D (Deuterium, 1%-100% enrichment of deuterium is incorporated), F, Cl;
$R_2$ is D, Cl;
$R_3$ is H, D;
$R_4$ and $R_5$ are D, H;
$R_6$, $R_9$ and $R_{10}$ are D, H;
$R_7$ is CN;
$R_8$ is F;
$R_{11}$, $R_{12}$, $R_{17}$, $R_{18}$, and $R_{19}$ are D;
$R_{13}$, $R_{14}$, $R_{15}$, $R_{16}$,
$R_{20}$ is D;
and salts thereof.

One of the objectives of the present invention is to provide deuterium enriched compounds of formula I or a pharmaceutically acceptable salt thereof.

It is another objective of the present invention to provide pharmaceutical compositions comprising a pharmaceutically acceptable carrier and a therapeutically effective amount of at least one of the deuterium enriched compounds of the present invention a pharmaceutically acceptable salt thereof.

It is another object of the present invention to provide a method for treating pulmonary arterial hypertension, hypertension, angina pectoris, and congestive heart failure, comprising administering to a host in need of such treatment a therapeutically effective amount of at least one of the compounds of the present invention or a pharmaceutically acceptable salt thereof.

It is another object of the present invention to provide a novel deuterium-enriched pyrimidine compounds of formula I, pharmaceutically acceptable salts thereof for use as therapeutic agents.

It is another objective of the present invention to provide the use of a novel compound of formula I or a pharmaceutically acceptable salt thereof for the manufacture of a medicine for the treatment of pulmonary arterial hypertension, resistant hypertension, hypertension, congestive heart failure, and male erectile dysfunction.

The present invention relates to compounds of formula I, their pharmaceutically acceptable salts, compositions and their use as mono therapy for treating, or preventing pulmonary arterial hypertension, pulmonary hypertension associated with chronic obstructive pulmonary disease (COPD), resistant hypertension, hypertension, congestive heart failure and erectile dysfunction, Alzheimer's disease, and age-related cognitive and memory dysfunction and cognitive and memory impairment associated with schizophrenia. The compounds of formula I may be given as therapy alone or in combination with existing therapies. These compounds may also have applications in the treatment of gastrointestinal disorders including irritable bowel syndrome, gastroesophageal reflux disease, emesis, nausea, vomiting, non-ulcer dyspepcia, anxiety, depression, pain, migraine, urinary incontinence, arterial fibrillation, arrhythmia, ischemic stroke, gastric emptying disorders, gastritis, gastrointestinal disorders, feeding disorders, obesity, anorexia, constipation, constipation, and respiratory depression.

Deuterium (D or $^2H$) is a stable isotope non-radioactive isotope of hydrogen (H) and has an atomic weight of 2.0144. Hydrogen occurs naturally as a mixture of the isotopes $^1H$, D (H2), and T (3H or tritium) and the natural abundance of deuterium is 0-015%. One of ordinary skill in the art recognizes that in all compounds containing H atom, H actually represents a mixture of H and D, with about 0-015% of D. So, compounds with a level of D that has been enriched to be greater than its natural abundance of 0.015%, should be considered unnatural and as a result novel as compared to their corresponding non-enriched counterparts.

The carbon-hydrogen bonds contain a naturally occurring distribution of hydrogen isotopes, namely $^1H$ or protium (about 99.9844%), $^2H$ or deuterium (D) (about 0.0156%), and $^3H$ or tritium (in the range between about 0.5 and 67 tritium atoms per $10^{18}$ protium atoms). Higher levels of deuterium incorporation produce a detectable Kinetic Isotope Effect (Werstiuk, N. H.; Dhanoa, D. S.; Timmins, G. Can J. Chem. 1979, 57, 2885; Werstiuk, N. H.; Dhanoa, D. S.; Timmins, G. Can J. Chem. 1983, 61, 2403), that could improve the pharmacokinetic and/or toxicologic parameters of compounds of formula I in comparison to compounds having naturally occurring levels of deuterium and their corresponding hydrogen (protium) analogs. The present invention disclosed herein describes novel compounds of formula I containing higher content of deuterium (>1%), synthesis and uses thereof as 5-HT$_{2B}$ receptor antagonists and/or inverse agonist for the treatment of central nervous system diseases including pulmonary arterial hypertension, resistant hypertension, hypertension, congestive heart failure and erectile dysfunction, Alzheimer's disease, Parkinson's disease, anxiety, depression, schizophrenia, insomnia, nausea, emesis, epilepsy pulmonary arterial hypertension, resistant hypertension, hypertension, congestive heart failure and erectile dysfunction pulmonary arterial hypertension, resistant hypertension, hypertension, congestive heart failure and erectile dysfunction pulmonary arterial hypertension, resistant hypertension, hypertension, congestive heart failure and erectile dysfunction, pain and others. Suitable modifications of certain carbon-hydrogen bonds into carbon-deuterium bonds generates novel substituted pyrimidine compounds with unexpected and non-obvious improvements of pharmacological, pharmacokinetic and toxicological properties in comparison to the non-isotopically enriched 5-HT2B antagonists, agonists, or inverse agonists. This invention relies on the judicious and successful application of chemical kinetics to drug design. Deuterium incorporation levels in the compounds of the invention are significantly higher than the naturally-occurring levels and are sufficient to induce at least one substantial improvement as described herein. All percentages given for the amount of D present are mole percentages.

"Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%.

It can be a significant synthetic challenge to produce 100% deuterium at a specific site of a compound. When 100% deuteration is recited or a deuterium atom is specifically shown in a chemical structure of a compound, a small amount of deuterium may still be present. Higher levels of deuterium content in a compound can be produced either by Hydrogen-Deuterium (H-D) exchange or by synthesizing the compound for specific deuteration. The H-D exchange is readily achieved in case of H atoms attached to heteroatoms for example in cases of carboxylic acids (COOH), sulfonamides (SO$_2$NH$_2$), alcohols (OH), basic amines (NH$_2$), etc. However, these incorporated D attached to hetero atoms (O, N, S) etc, readily revert back to H upon exposure to water or any acidic compounds containing H atoms. The preferred deuterium containing compounds are the ones which contain D directly attached to carbon atoms of the structure of the compounds of this invention.

In some embodiments, the deuterium enrichment in the compounds of the present invention is greater than 4%, 5%, 6%, 7%, 8%, 9% or 10%. In other embodiments, the deuterium enrichment in the compounds of the present invention is greater than 20%. In further embodiments, the deuterium enrichment in the compounds of the present invention is greater than 50%. In some embodiments, the deuterium enrichment in the compounds of the present invention is greater than 70%. In some embodiments, the deuterium enrichment in the compounds of the present invention is greater than 90%.

The examples provided in the definitions present in this application are non-inclusive unless otherwise stated. They include but are not limited to recited examples. The compounds of the present may have various isomers including all stereoisomers of asymmetric atoms and geometric, tautomeric or rotamers, and all isomers are considered to be part of the present invention. All processes used to prepare compounds of the present invention and intermediates made therein are considered to be part of the present invention.

"Pharmaceutically acceptable salts" refer to derivatives of the disclosed compounds wherein the parent compound is modified by making acid or base salts thereof. Examples of the pharmaceutically acceptable salts include, but not limited to, mineral or organic acid salts of the basic residues. The pharmaceutically acceptable salts include but not limited to HCl, HBr, HI, acetic, trifluoroacetic, citric, ascorbic, benzoin, methanesulfonic, benzenesulfonic, bicarbonic, carbonic, ethane disulfonic, edetic, fumaric, maleic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, tolouenesulfonic, and p-bromobenzenesulfonic.

The preparation of pyrimidine compounds of formula I are illustrated in schemes 1-8 below and in the examples given in Table 1. The schemes and examples are given for the purpose of illustrating the invention and not for limiting the scope or spirit of the invention.

Step A: To a solution of acetaldehyde-d$_4$ 1 (1.2 g) in toluene is added 1.2 equivalent of ethyl cyanoacetate (3.2 g) and ammonium acetate (2.2 g) followed by acetic acid (15 mL). The mixture is refluxed for 6 h under nitrogen using Dean-Stark apparatus. After cooling to room temperature by allowing it to stand, the reaction mixture is concentrated using rotary evaporator under vacuum to remove solvent. To the concentrated residue, is added water and the adduct product 2 is extracted with ethyl acetate. The combined organic layer is dried over anhydrous sodium sulfate or anhydrous magnesium sulfate and concentrated under vacuum. The resulting product 2 (3.0 g) obtained as such is used in step B.

Step B: Morpholine is added to 2 (3 g) in ethanol (5 mL) followed by addition of sulfur in slight excess under nitrogen atmosphere and the suspension is refluxed with stirring for 12 h. After cooling to room temperature, the reaction mixture is concentrated in vacuum and the product 3 is extracted with ethyl acetate from aqueous phase. The combined organic layer was dried over anhydrous sodium sulfate, filtered and the filtrate is concentrated in vacuum and then purified by flash column chromatography using mixture of ethyl acetate and hexane to yield Ethyl 2-Aminothiophene-3-carboxylate-d$_2$ 3 (2.6 g). Mass spectral analysis (MS): m/z: 173.5.

Step C: The ester 3 (0.88 mg) is heated at reflux with deutero ammonium acetate-d$_1$ (100 mg) in 3 ml of formic acid for 8 hrs. The mixture is poured onto ice and the resulting material is filtered and recrystallized from acetone water to give hydroxypyrimidine 4 (0.6 g). Mass spectral analysis (MS): m/z 155.

Step D: The deuterothienopyrimidinol 4 (2 mmol) is heated in thionyl chloride with catalytic amount of N,N-dimethylformamide for 5 hours. The mixture is allowed to cool to room temperature and the excess thionyl chloride is removed under reduced pressure. Excess of ice is added to the mixture and product extracted with dichloromethane. The extracts are dried with anhydrous sodium sulfate, filtered, concentrated and the product purified by flash chromatography over silica gel to yield 5 (0.5 g). Mass spectral analysis (MS): m/z 173.

Step E: To a solution of pyrimidine derivative 5 (0.5 g) was added deuterated acetic acid-$d_4$ (20 mL) and N-chlorosuccinimide (0.2 g) and the mixture was heated for 2.5 h. The reaction mixture was cooled to room temperature and removed acetic acid-$d_4$ in vacuum and the residue was treated with aqueous sodium hydroxide and extracted with dichloromethane. The combined organic extracts were dried over anhydrous MgSO4, filtered and concentrated before purification by flash column chromatography to isolate the 2,6-dichlorothienopyrimidine 6 (0.4 g). Mass spectral analysis (MS) m/z: 205.9.

reaction mixture is cooled to room temperature and poured over to ice. The compound is extracted with methylene chloride and the extracts are dried over anhydrous magnesium sulfate or sodium sulfate, filtered and concentrated under vacuum. The crude product is purified by flash column chromatography to give 8 (0.62 g). MS: m/z 90 (M+1).

Step G: Methyl thioglycolate (1.1 g) and sodium methoxide (2 equiv) in methanol are added to 8 (0.62 g) and the mixture refluxed for 6 hours. The mixture is cooled to room temperature, concentrated to remove solvent and the resulting mixture partitioned between methylene chloride and water. The aqueous portion is further extracted with dichloromethane and ethyl acetate. The combined organic extracts Scheme 1:

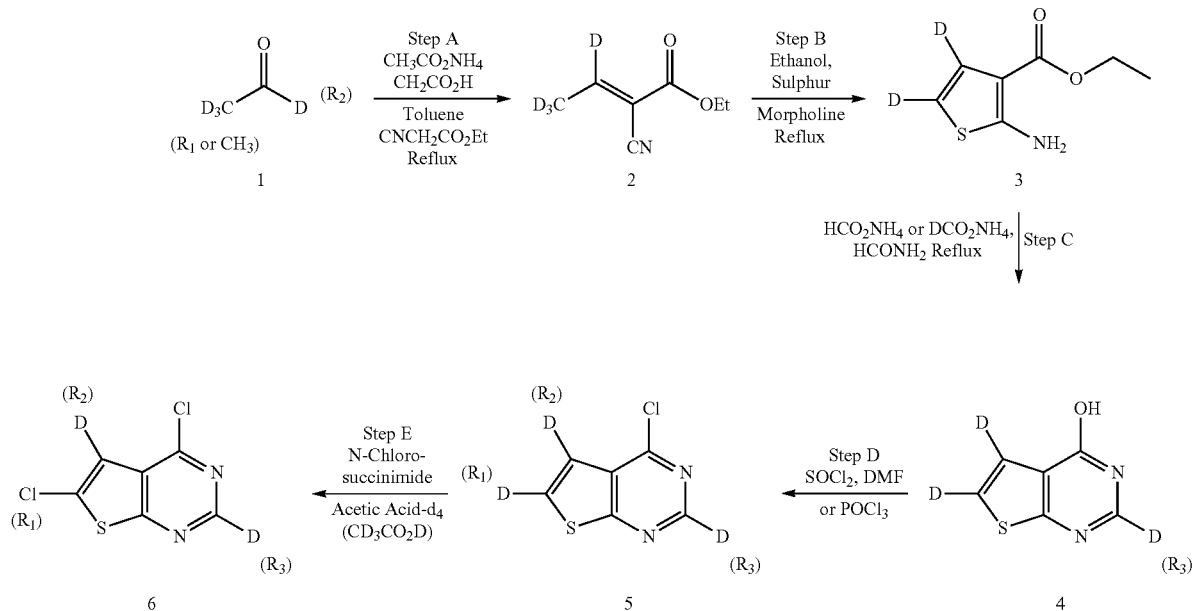

The regioisomeric thienopyrimidine 12 is prepared from deuterated acetaldehyde-d4 as illustrated in Scheme 2.

Step F: To acetaldehyde 7 (0.48 g), DMF, and phosphorus oxychloride (1.2 equiv) is added and the mixture stirred for 5 minutes. Hydroxylamine (1.2 equivalent) is added to the reaction mixture and heated at 50 degree C. for 5 hours. The are dried over anhydrous sodium sulfate, filtered and concentrated to a residue. Flash column chromatography of the residue afforded an amino ester 9 (0.8 g).

The intermediate 9 was converted to the pyrimidine derivatives 10, 11 and 12 by using methods describes in Step C, Step D, and Step E, respectively.

Scheme 2:

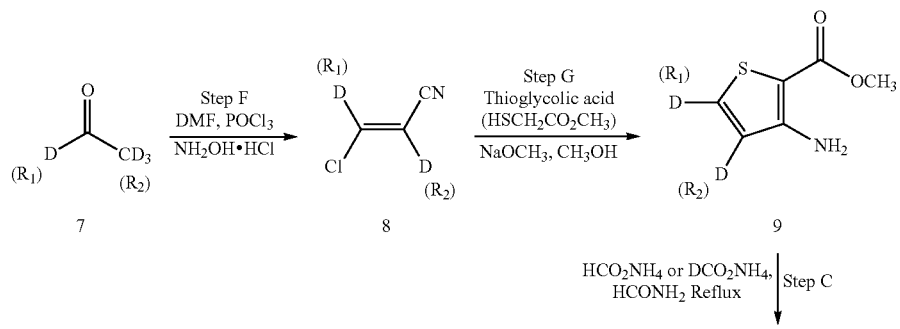

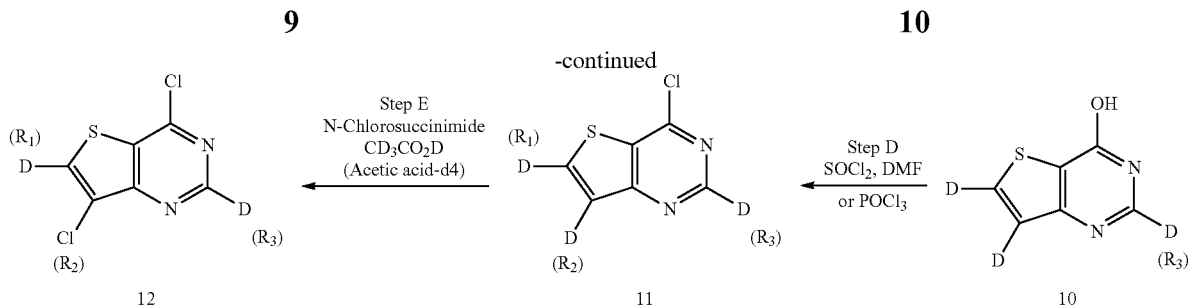

Similarly, the amino ester of thiazole, 13, was converted to the 4-hydroxythiozolylpyrimidine 14 and 4-chlorothiazolylpyrimidine 15 as illustrated in Scheme 3 below using step C and Step D as described above.

Scheme 3:

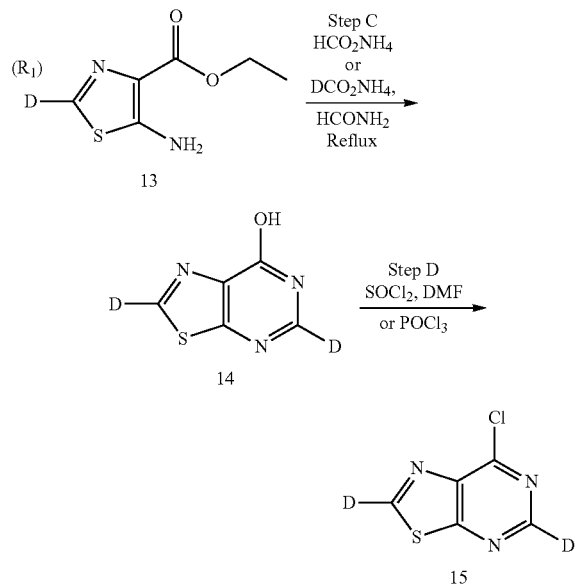

Furthermore, the regioisomeric thiazolylpyrimidine 18 is prepared from the corresponding deuterated amino ester 16 as illustrated in Scheme 4 below by utilizing the reaction steps C and D.

Scheme 4:

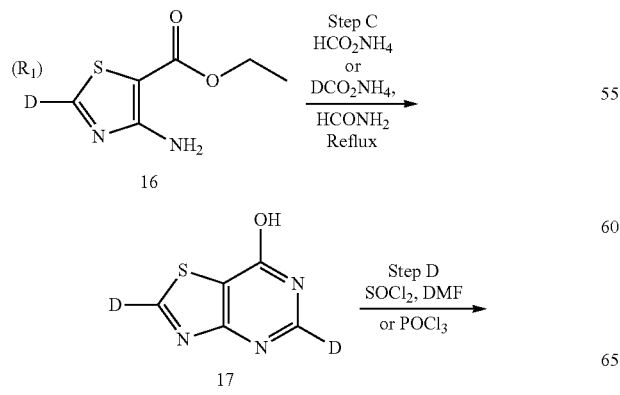

Step F: One of three key building blocks of the compounds of formula I of the present invention is the partially or fully deuterated 4-N-Boc-aminopiperidine 20. The preparation of 20 is illustrated in scheme 5 below that employs the use of the reaction step F. The 4-N-Boc-piperidinone is converted to the corresponding amine by reductive amination of 19 with ammonium acetate ($NH_4OAc$) using either sodium triacetoxy borodeuteride [$NaBD(OAc)_3$], or sodium borotetradeuteride [$NaBD_4$], or sodium cyanoborodeuteride [$NaBD_3CN$], as reducing agents in dicholoroethane or dicholoromethane or DMF or tetrahydrofuran (THF) and water ($H_2O$). To a solution of 0.2 g of 4-N-Boc-(2,2,6,6-tetradeuteropiperidinone) 19 ($R_{11}, R_{12}, R_{17}, R_{18}$ are D; $R_{13}, R_{14}, R_{15}, R_{16}$ are 14) in DCE and AcOH is added [2 equiv of $NaBD(OAc)_3$] and the reaction mixture stirred for 2 h. The mixture was concentrated and basified with $NaHCO_3$ and saturated with NaCl and the resulting mixture is extracted with methylene chloride. The organic solvent extracts were concentrated in vacuo and the product isolated by flash column chromatography to yield 20 (0.12 g).

Scheme 5:

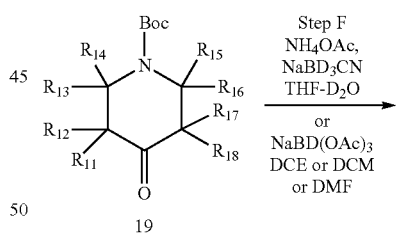

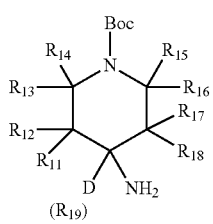

Ac = $COCH_3$ (Acetyl)
DCE = Dichloroethane
DCM = Dichloromethane
DMF = N,N-Dimethylformamide Step G: Diisopropyl ethylamine (Hunigs base) is added to a solution of 4-N-Boc-aminopiperidine-$d_5$, 20 (0.22 g) in acetonitrile (3 ml) followed by addition of 6 (1 equiv). The reaction mixture is refluxed for 24 h. Acetonitrile is removed in vacuo and the resulting residue is dissolved in ethyl acetate (25 ml) and the solution washed with aqueous (aq.) saturated solution of sodium bicarbonate and saturated aqueous solution of sodium chloride (brine). The organic phase is dried over anhydrous $MgSO_4$, concentrated in vacuo and purified by flash column chromatography to give N-Boc protected 21, which in turn is treated with TFA in $CH_2Cl_2$ for 2-3 h or with HCl in ether for 12 h to give the crude amine 21. The mixture containing 21 is concentrated in vacuo, treated the residue with aqueous $NaHCO_3$ solution and aqueous solution of NaCl. The organic product was extracted with ethyl acetate and dicholoromethane and the combined organic solvent extracts washed with brine, dried over anhydrous $MgSO_4$, filtered and concentrated in vacuo. The resulting material is purified to afford 21 (0.15 g). MS: m/z 276 (M+1).

Similarly, the regioisomeric thienopyrimidine 22 (m/z 276 M+1) is prepared from 12 and 20 by using Step H. The regioisomeric thiazolylpyrimidines, 23 (m/z 278 M+1) and 24 (m/z 278 M+1) are also prepared in a similar manner by using Step I and Step J from their precursors 15 and 20, and 18 and 20, respectively as illustrated in Scheme 6.

Scheme 6:

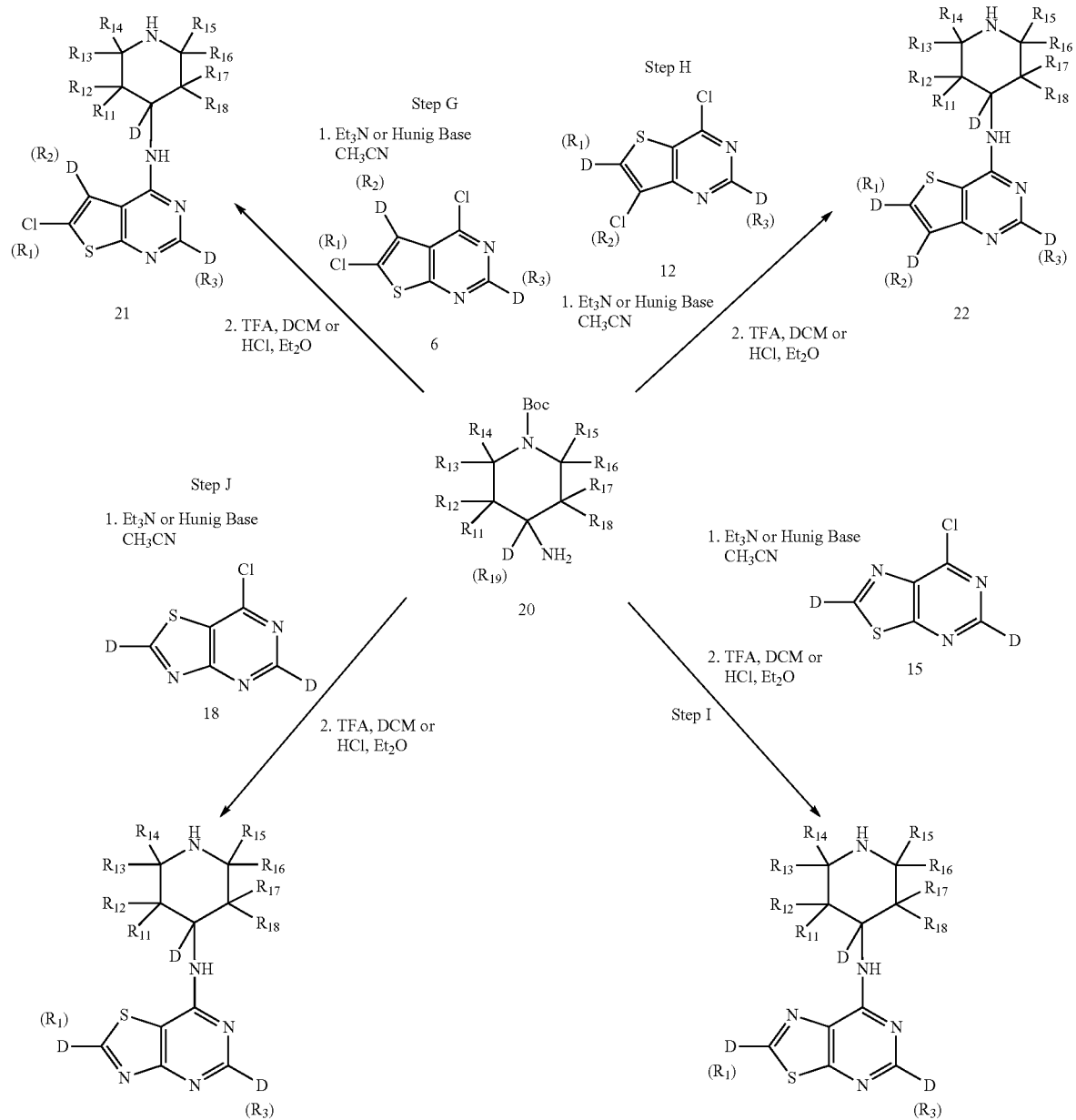

Step K: The 4-aminopiperidine-2-chlorothienopyrimidines 21 and 22 are also prepared from the corresponding N-Boc derivatives 25 and 26, respectively as shown in Scheme 7 by step K as described in Step E of scheme 1.

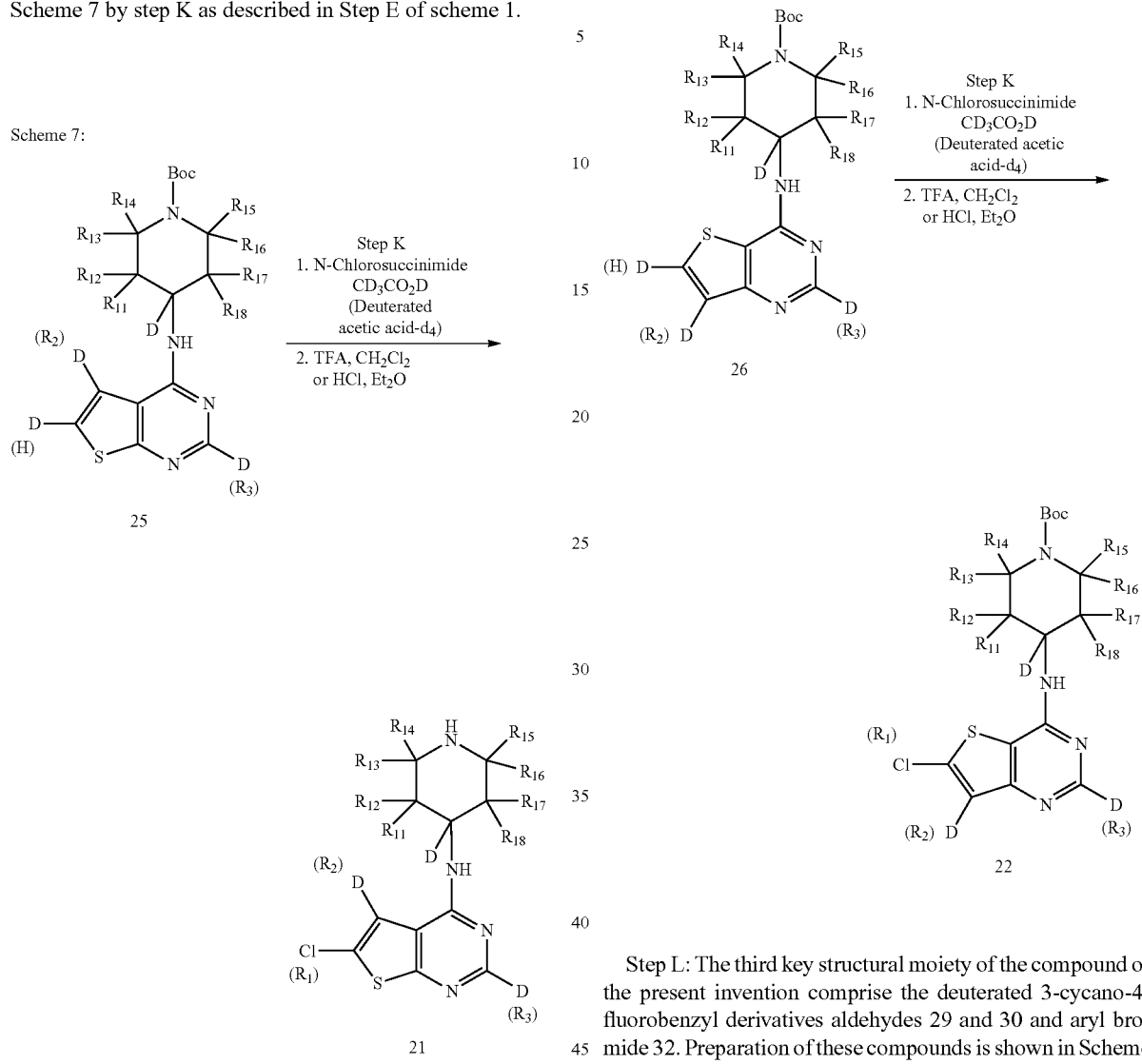

Step L: The third key structural moiety of the compound of the present invention comprise the deuterated 3-cycano-4-fluorobenzyl derivatives aldehydes 29 and 30 and aryl bromide 32. Preparation of these compounds is shown in Scheme 8 below.

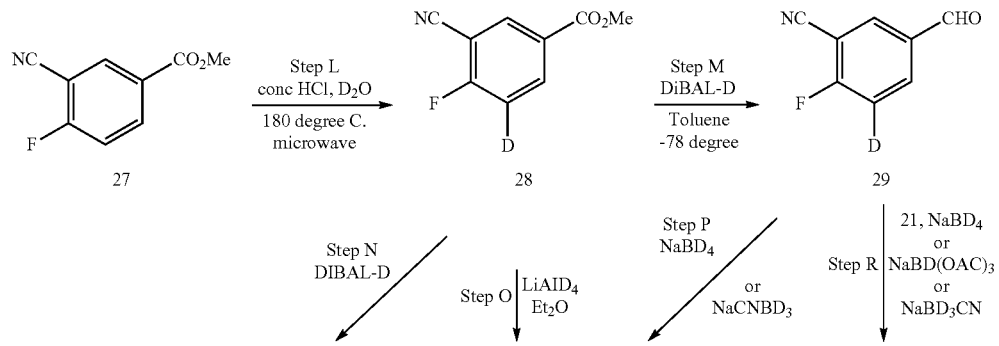

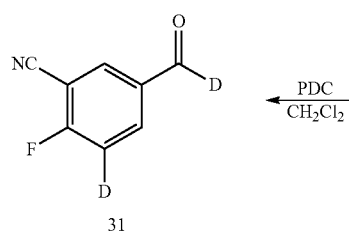
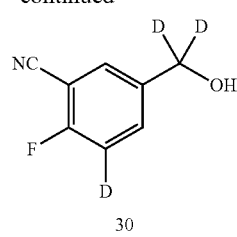
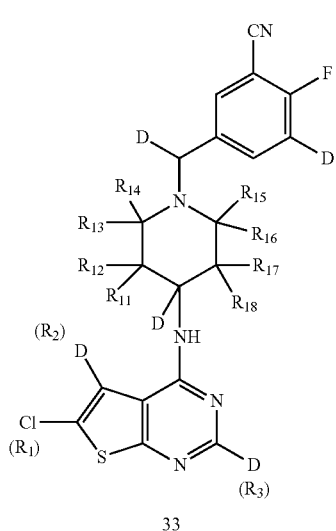
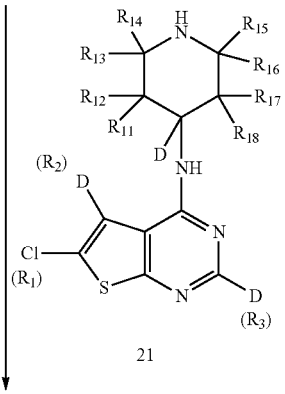
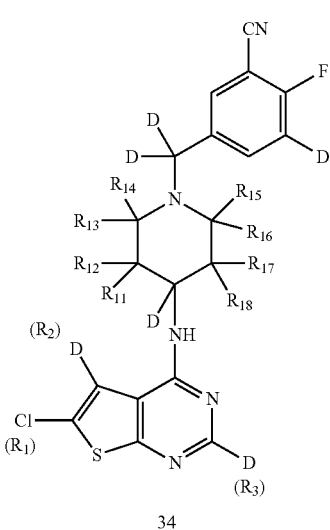
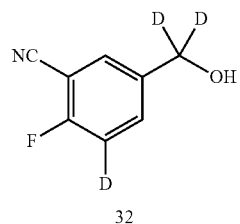
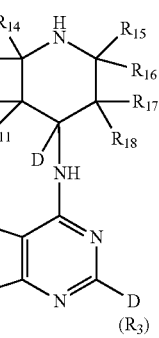

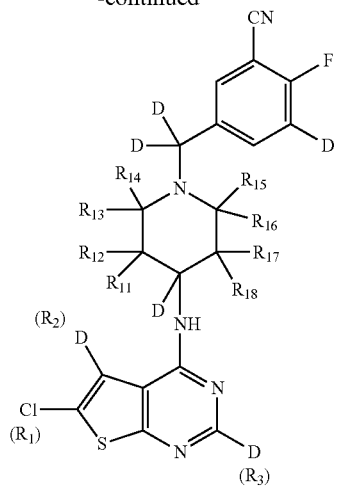

34

Methyl 3-cyano-4-fluorobenzoate 27 (1.8 g) is deuterated by heating with 1 equiv of $D_2O$ and conc. HCl at 180 degree C. under microwave irradiation for 30 minutes (Martin A.; Lautens M., Org. Lett. 2008, 10, 4351-4353). The reaction mixture is basified with aqueous solution of $NaHCO_3$ and extracted with ether. The combined ethereal extracts are concentrated, dried, filtered to and concentrated in vacuo. The concentrated oil is flash chromatogarphed to afford the mono-deuterated 28 (1.62 g).

28 is converted to aldehyde 29 by reducing with diisobutyl aluminum hydride (DIBALH) or diisobutyl aluminum deuteride (DIBALD) in toluene and converted to 31 by treating 28 with DIBALD in toluene at −78 C.

Step M: To a toluene solution of deuterated ester 28 (0.8 g) cooled to −78 C by placing the reaction flask in dry ice-acetone mixture, is added 1.1 equiv of DIBALH or DIBALD and the mixture stirred for 1 hour and quenched methanol and sodium hydroxide. The aqueous phase is extracted with solvent mixture of ether and ethyl acetate, dried extracts over $MgSO_4$, filtered and concentrated in vacuo to an oil which after flash column chromatography gave 29 (0.53 g).

Step N: To a solution of deuterated ester 28 (0.8 g) in toluene cooled to −78 C is added 1.1 equiv of DIBALD and the mixture stirred for 1 hour. Methanolic sodium hydroxide is added to reaction mixture and the aqueous phase is extracted with solvent mixture of ether and ethyl acetate, dried extracts over $MgSO_4$, filtered and concentrated in vacuo to an oil which after flash column chromatography gave 31 (0.55 g).

Step O: To a solution of deuterated ester 28 (0.8 g) in ether cooled to −78 C is added 1.1 equiv of $LiAlD_4$ and the mixture stirred for 1 hour. Aqueous NaOH is added to reaction mixture and stirred for 3o min and then the aqueous phase is extracted with ether and ethyl acetate, dried extracts over $MgSO_4$, filtered and concentrated in vacuo to an oil which after flash column chromatography gave 30 (0.5 g).

Step P: To a solution of 29 (0.5 g) in THF cooled to −78 C is added 1.2 equiv of $NaBD_4$ and the mixture stirred for 1 hour. Methanolic sodium hydroxide is added to reaction mixture and the aqueous phase is extracted with ether and ethyl acetate, dried extracts over anhydrous $MgSO_4$, filtered and concentrated in vacuo to an oil which after flash column chromatography afforded 30 (0.36 g).

Step Q: To a solution of 30 (0.86 g) in dichloromethane at 0 degree is added carbon tetrabromide (1.1 equiv) and stirred. After 5 min, triphenyl phosphine (1 equiv) is added and the resulting mixture stirred for 1 h at 0 degree and allowed to warm to room temperature. The mixture treated with methanol and the mixture concentrated in vacuo, then purification by flash column chromatography gave the tri-deuterated aryl bromide 32 (0.66 g).

The substituted deuterated benzyl bromide 30 can also be converted to the corresponding deuterated aldehyde 31 by its oxidation with PDC (pyridinium dichromate) in methylene chloride in the presence of dry molecular sieves.

Step R: To a mixture of 21 (0.3 g) and deuterated aldehyde 29 is added DCE and $NaBD(OAc)_3$ (1.5 equiv) and deuterated acetic acid-$d_4$(2 equiv). The reaction mixture is stirred for 12 h at room temperature before the addition of aqueous $NaHCO_3$ solution. The product is extracted with ethyl acetate, dried over anhydrous MgSO4, filtered and concentrated in vacuo to give an oil which is then purified by flash column chromatography to yield the final compound 33 (0.36 g).

The compound 34 is prepared from the aldehyde 31 by using the procedure described in step R.

Step S: To a solution of 21 (0.28 g) and 0.4 ml of di-isopropylethylamine (Hunigs base) in 3 ml of $CH_3CN$ is added 32 and the resulting mixture was heated at 85° C. with stirring for 12 h. The mixture is cooled to room temperature and poured over to aqueous sodium bicarbonate solution. The mixture is extracted with ethyl acetate and the combined organic extracts are dried over sodium sulfate, filtered and concentrated in vacuo. The residue is purified by flash column chromatography to give 34 (0.3 g).

To prepare the fully deuterated (or per-deuterated) aldehyde or bromide analogs of 29, 31 and 32, the fully deuterated precursor 38 is prepared from the corresponding aniline 35 as illustrated in Scheme 9 below.

Step T: Methyl 3-amino-4-fluorobenzoate 35 (1.7 g) is heated with 1 equiv of cone HCl and $D_2O$ at 180° C. under microwave irradiation for 30 minutes. The mixture is cooled to room temperature and treated with methanol and basified with aqueous solution of $NaHCO_3$. The mixture is extracted with ether/ethyl acetate mixture, washed combined organic extracts with brine, dried over sodium sulfate, filtered and concentrated in vacuo. The crude product is purified by flash column chromatography to yield di-deuterated aniline 36 (1.3 g).

Step U: The deuterated aniline 36 (1.3 g) is diazotized by treating it with sodium nitrite (1.1 equiv) in the presence of sulfuric acid at 0° C. for 6 hours. The diazonium salt intermediate is treated with potassium cyanide (1 equiv) at 0° C. to room temperature for 6 hours. Aqueous $NaHCO_3$ solution is added to the reaction mixture slowly and then extracted with solvent mixture of ether/ethyl acetate. The combined extracts are dried over anhydrous sodium sulfate, filtered and concentrated in vacuo. The product is isolated by purification of the residue by flash column chromatography to afford the nitrile 37 (0.9 g).

Using the microwave irradiation method as described in step T, 37 (0.9 g) is converted into 38 (0.65 g) by substituting deuterium ortho to fluorine substituent at the benzene ring of 38.

38 is then converted to the corresponding aldehydes and bromide as described for 27 in Scheme 8 to couple with 21 to produce the deuterated derivatives of pyrimidines 33 and 34.

All compounds of formula I containing deuterated N-D group is prepared from the corresponding N—H containing precursor by treating N—H precursor with deuterated methanol-$d_1$ ($CH_3OD$) or methanol-$d_4$ ($CD_3OD$) or deuterated acetic acid-$d_4$ ($CD_3CO_2D$).

The pharmaceutical salts including maleate, fumarate, acetate, mesylate, tartarate, citrate, HCl, etc., are prepared by treatment of the free bases e.g., 33 and 34 with appropriate acids in a suitable solvent such as ether. methanol, or methylene chloride, etc. followed by removal of the solvent in vacuo.

Scheme 9:

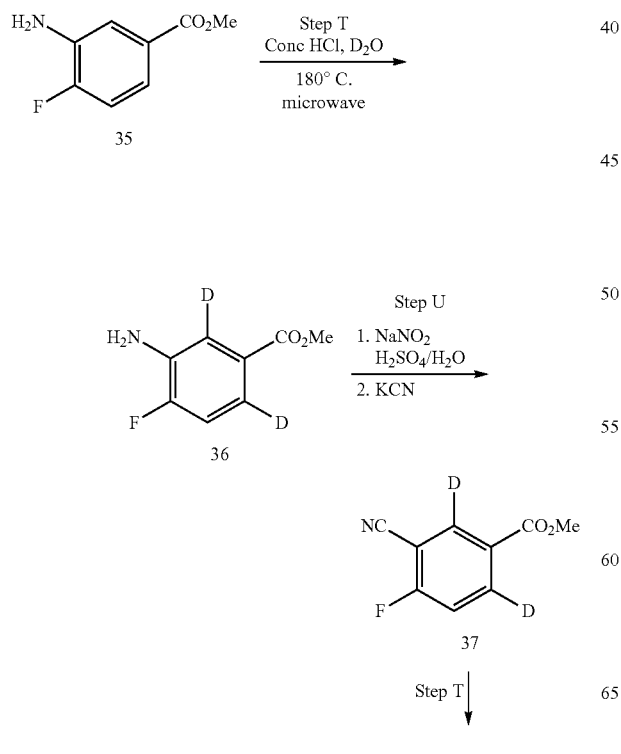

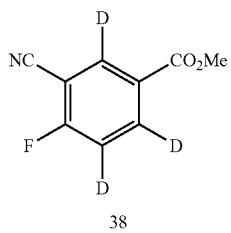

EXAMPLES

Given below are compounds that are representative examples of the present invention.

Example 1

N-(1-(3-Cyano-4-fluorobenzyl-$d_2$)piperidin-4-yl-$d_5$)-6-chlorothieno-$d_1$[2,3-d]pyrimidine-4-amine-$d_1$

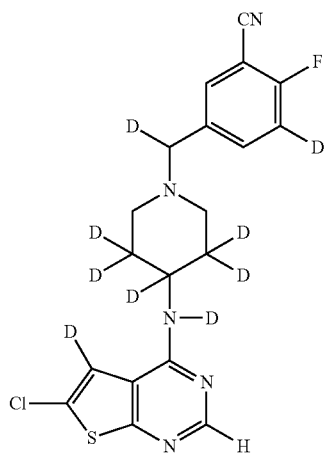

The title compound is prepared by using the methods described in scheme above. Mass spectral analysis (m/e): 411 (M+1).

Example 2

N-(1-(3-Cyano-4-fluorobenzyl-d$_4$)piperidin-4-yl-d$_5$)-6-chlorothieno-d$_1$[2,3-d]pyrimidine-4-amine-d$_1$

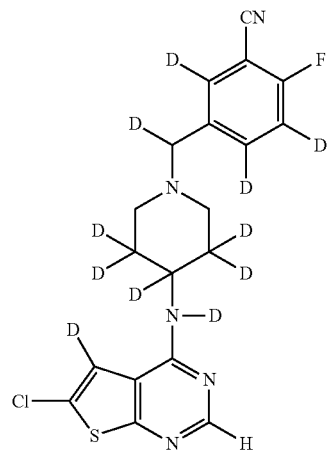

The title compound is prepared by using the methods described in scheme above. MS (m/e): 413 (M+1).

Example 3

N-(1-(3-Cyano-4-fluorobenzyl-d$_5$)piperidin-4-yl-d$_5$)-6-chlorothieno-d$_1$[2,3-d]pyrimidine-4-amine-d$_1$

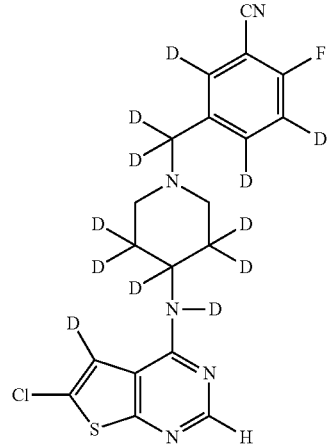

The title compound is prepared by using the methods described in scheme above. MS (m/e): 414 (M+1).

Example 4

N-(1-(3-Cyano-4-fluorobenzyl-d$_5$)piperidin-4-yl-d$_5$)-6-chlorothieno-d$_1$[2,3-d]pyrimidine-d$_1$-4-amine-d$_1$

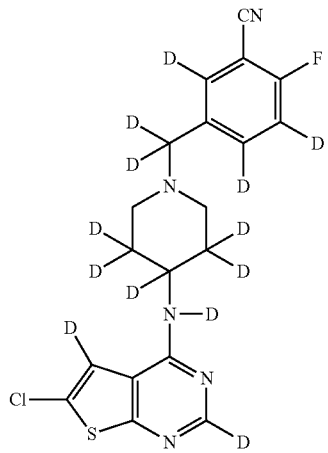

The title compound is prepared by using the methods described in schemes above. MS (m/e): 415 (M+1).

Example 5

N-(1-(3-Cyano-4-fluorobenzyl-d$_2$)piperidin-4-yl-d$_5$)-6-chlorothieno-d$_1$[3,2-d]pyrimidine-4-amine-d$_1$

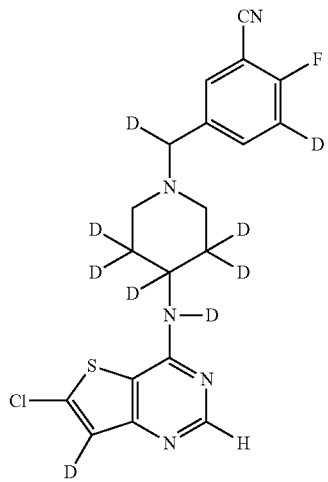

The title compound is prepared by using the methods described in scheme above. Mass spectral analysis (m/e): 411 (M+1).

Example 6

N-(1-(3-Cyano-4-fluorobenzyl-d$_4$)piperidin-4-yl-d$_5$)-6-chlorothieno-d$_1$[3,2-d]pyrimidine-4-amine-d$_1$

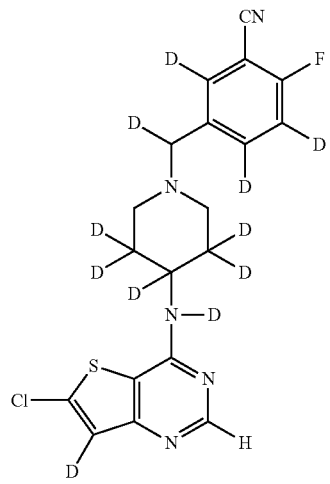

The title compound is prepared by using the methods described in scheme above. MS (m/e): 413 (M+1).

Example 7

N-(1-(3-Cyano-4-fluorobenzyl-d$_5$)piperidin-4-yl-d$_5$)-6-chlorothieno-d$_1$[3,2-d]pyrimidine-4-amine-d$_1$

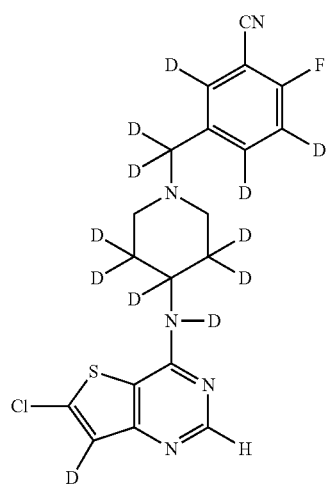

The title compound is prepared by using the methods described in scheme above. MS (m/e): 414 (M+1).

Example 8

N-(1-(3-Cyano-4-fluorobenzyl-d$_5$)piperidin-4-yl-d$_5$)-6-chlorothieno-d$_1$[3,2-d]pyrimidine-d$_1$-4-amine-d$_1$

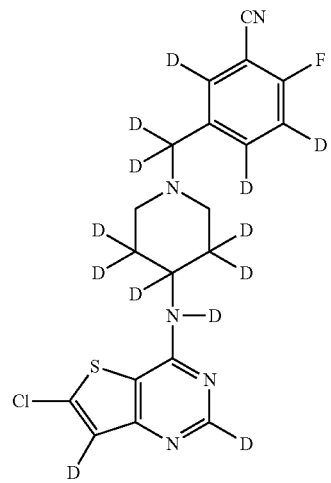

The title compound is prepared by using the methods described in scheme above. MS (m/e): 415 (M+1).

Example 9

N-(1-(3-Cyano-4-fluorobenzyl-d$_2$)piperidin-4-yl-d$_5$)-2-chlorothiazolo[5,4-d]pyrimidine-7-amine-d$_1$

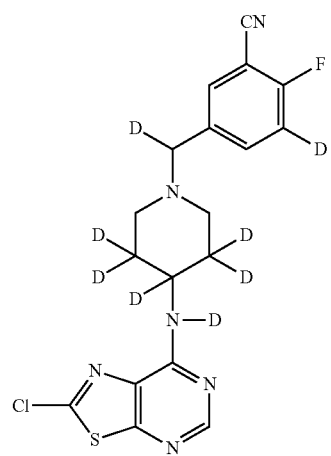

The title compound is prepared by using the methods described in scheme above. MS (m/e): 411 (M+1).

Example 10

N-(1-(3-Cyano-4-fluorobenzyl-d₄)piperidin-4-yl-d₅)-2-chlorothiazolo[5,4-d]pyrimidine-7-amine-d₁

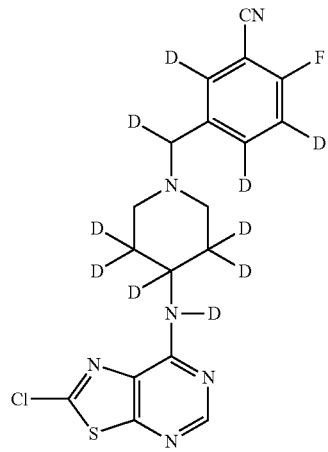

The title compound is prepared by using the methods described in scheme above. MS (m/e): 413 (M+1).

Example 11

N-(1-(3-Cyano-4-fluorobenzyl-d₅)piperidin-4-yl-d₅)-2-chlorothiazolo[5,4-d]pyrimidine-7-amine-d₁

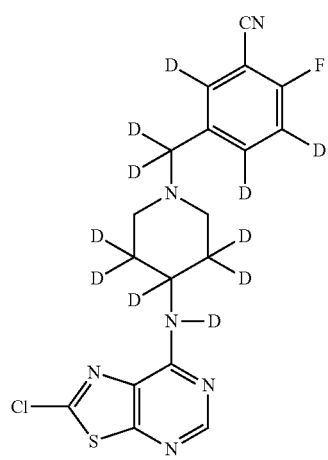

The title compound is prepared by using the methods described in scheme above. MS (m/e): 414 (M+1).

Example 12

N-(1-(3-Cyano-4-fluorobenzyl-d₅)piperidin-4-yl-d₅)-2-chlorothiazolo[5,4-d]pyrimidine-5-d₁-7-amine-d₁

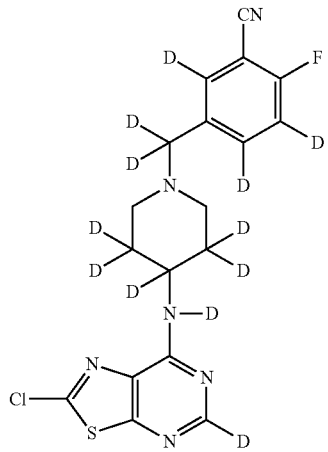

The title compound is prepared by using the methods described in scheme above. MS (m/e): 415 (M+1).

Example 13

N-(1-(3-Cyano-4-fluorobenzyl-d₂)piperidin-4-yl-d₅)-2-chlorothiazolo[4,5-d]pyrimidine-7-amine-d₁

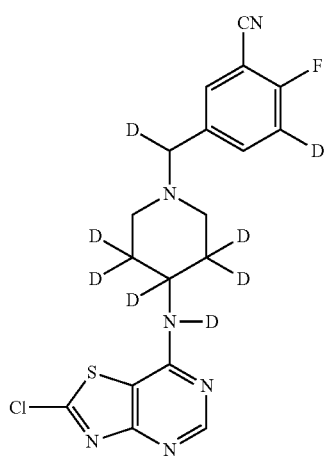

The title compound is prepared by using the methods described in scheme above. MS (m/e): 411 (M+1).

Example 14

N-(1-(3-Cyano-4-fluorobenzyl-d₄)piperidin-4-yl-d₅)-2-chlorothiazolo[4,5-d]pyrimidine-7-amine-d₁

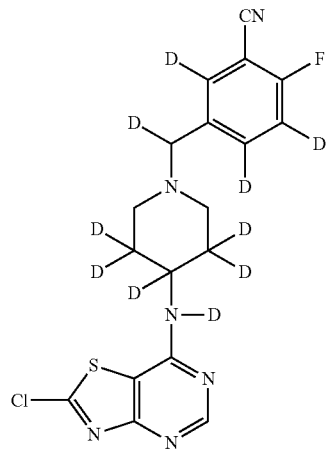

The title compound is prepared by using the methods described in scheme above. MS (m/e): 413 (M+1).

Example 15

N-(1-(3-Cyano-4-fluorobenzyl-d₅)piperidin-4-yl-d₅)-2-chlorothiazolo[4,5-d]pyrimidine-7-amine-d₁

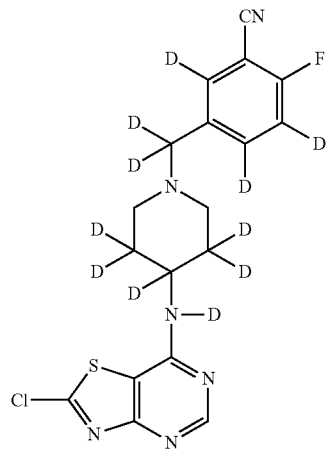

The title compound is prepared by using the methods described in scheme above. MS (m/e): 414 (M+1).

Example 16

N-(1-(3-Cyano-4-fluorobenzyl-d₅)piperidin-4-yl-d₅)-2-chlorothiazolo[4,5-d]pyrimidine-5-d₁-7-amine-d₁

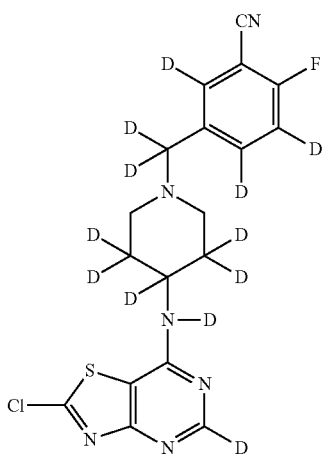

The title compound is prepared by using the methods described in scheme above. MS (m/e): 415 (M+1).

17

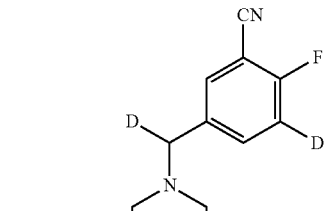
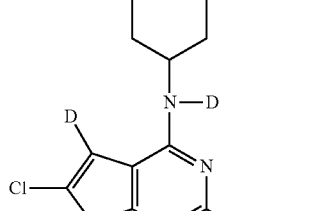

18

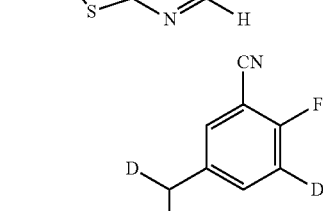
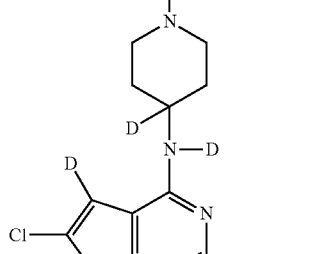

19
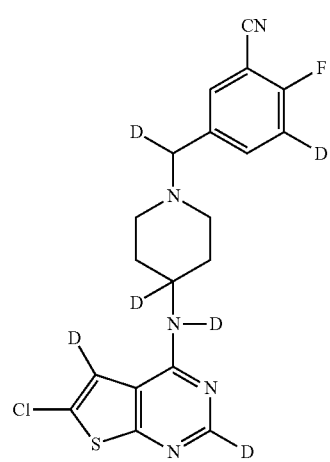
20
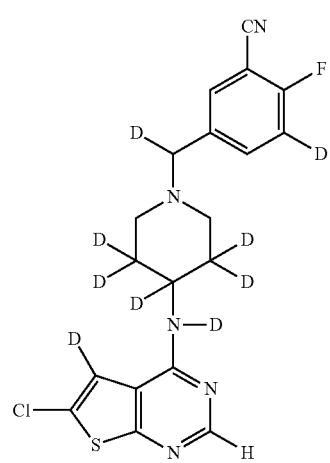
21
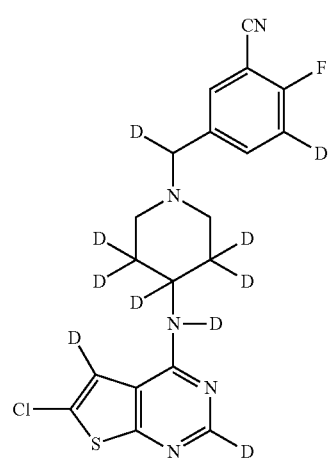
22
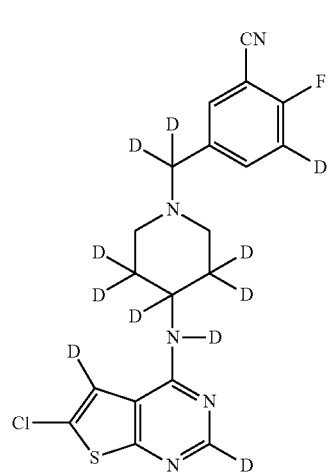
23
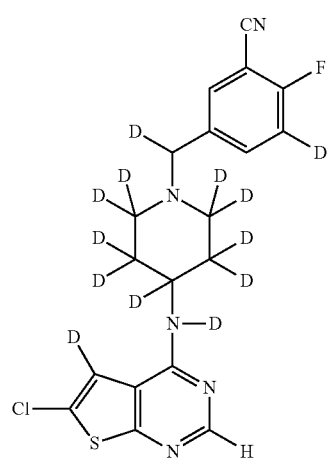
24
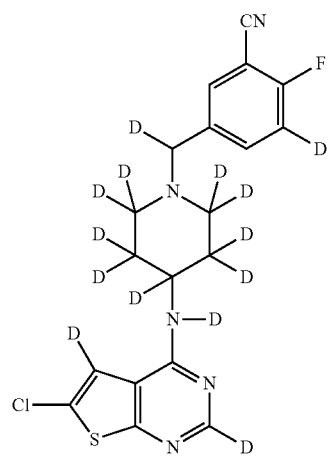

31
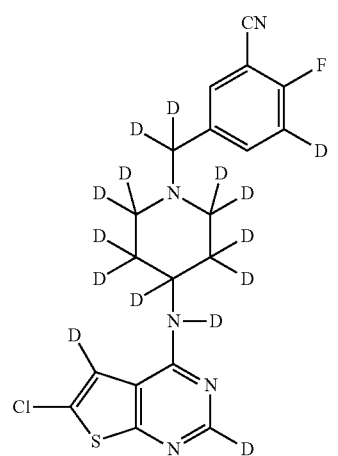
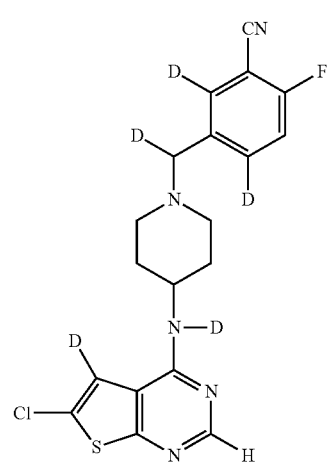
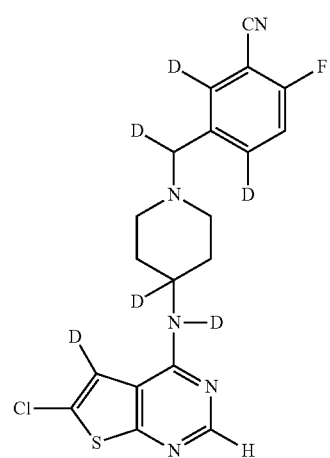
32
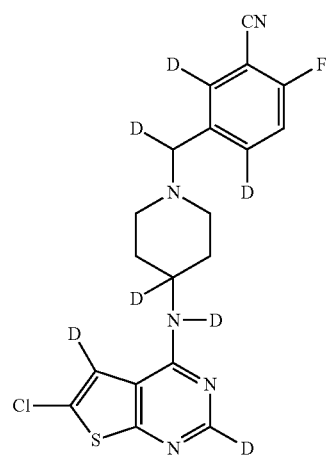
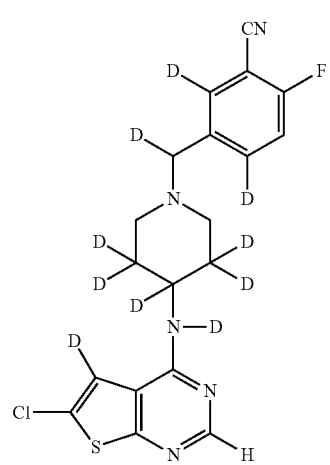
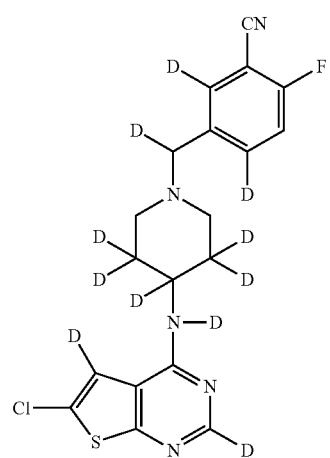

33
-continued
31
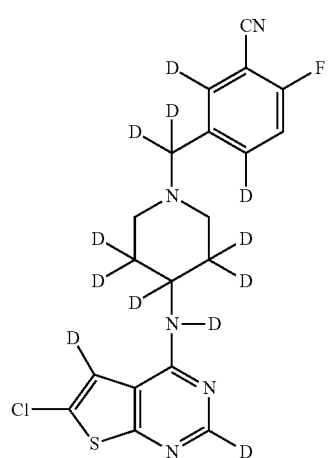
32
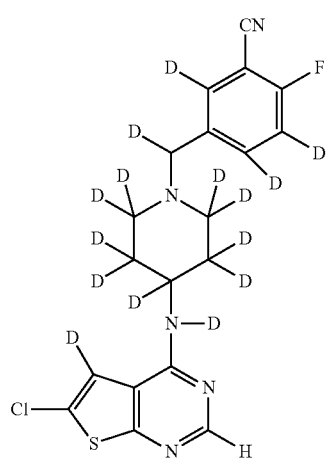
33
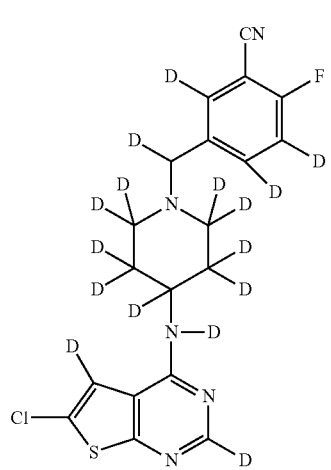
34
-continued
34
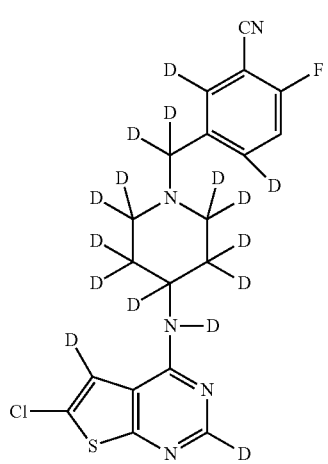
35
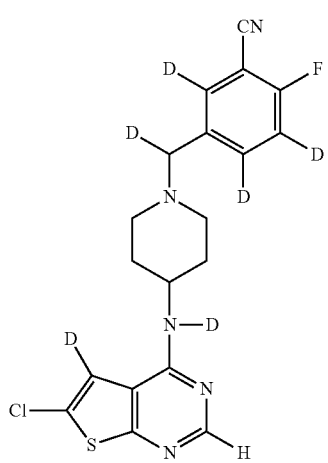
36
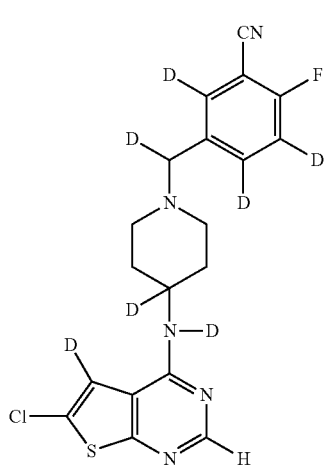

35
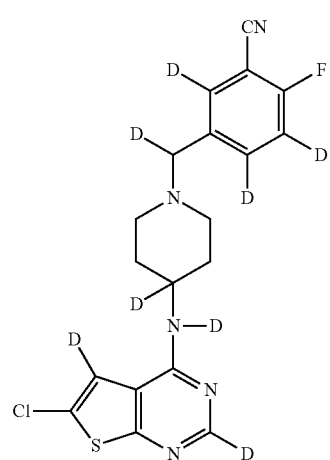
37
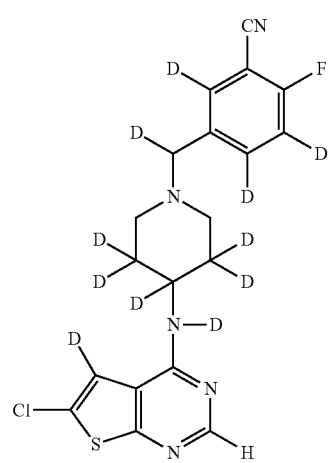
38
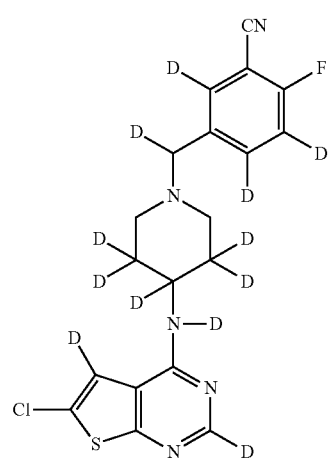
39
36
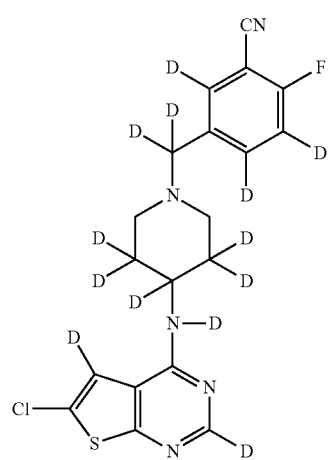
40
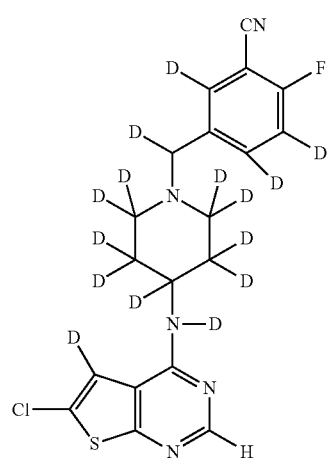
41
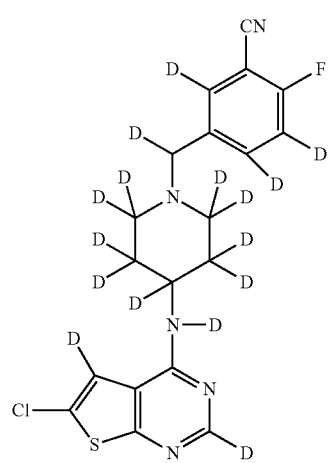
42

43
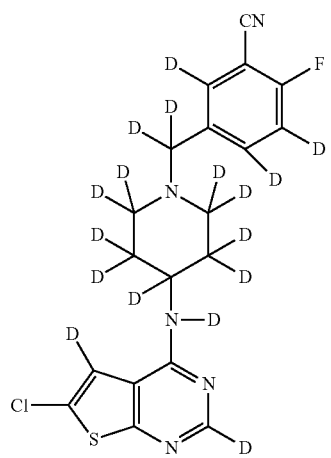
44
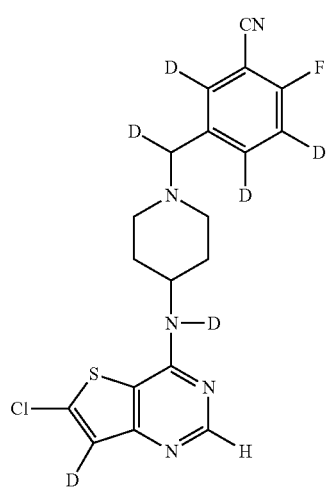
45
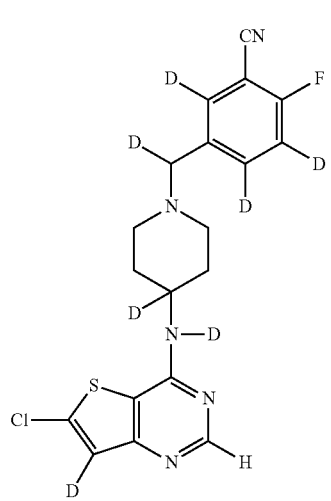
46
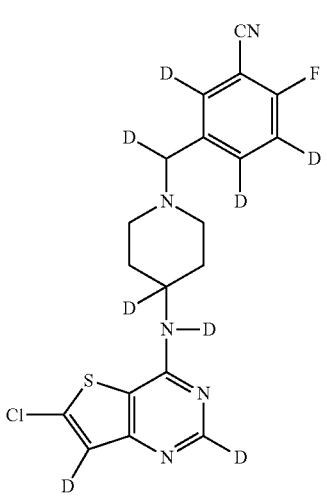
47
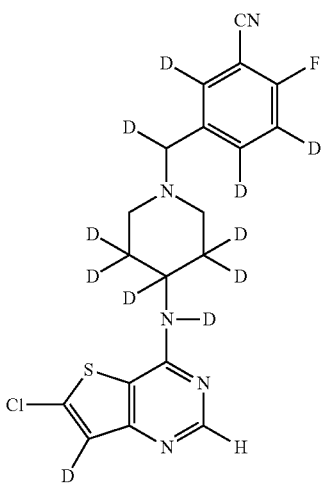
48
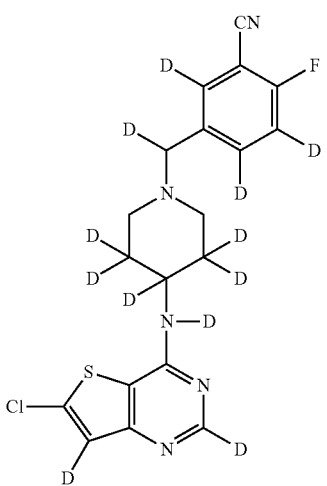

49
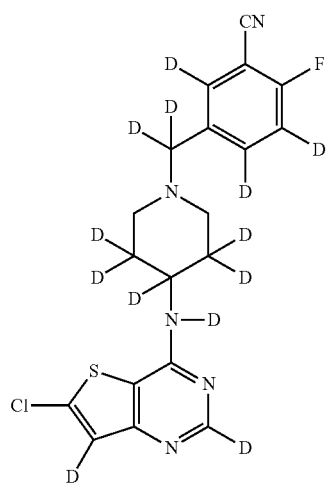
50
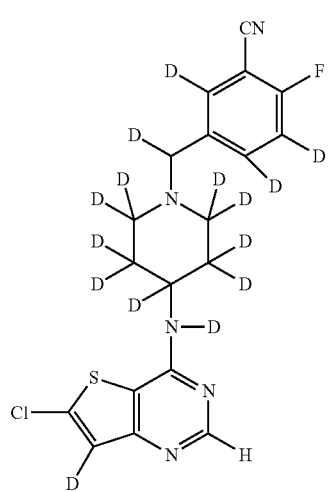
51
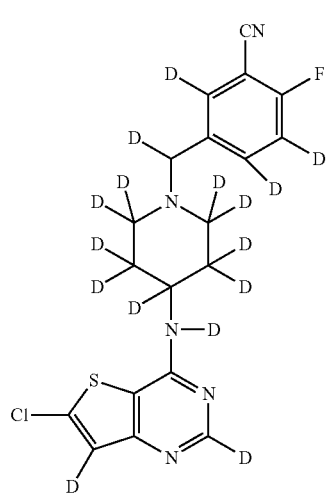
52
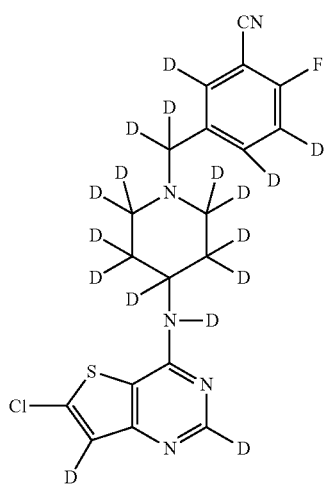
53
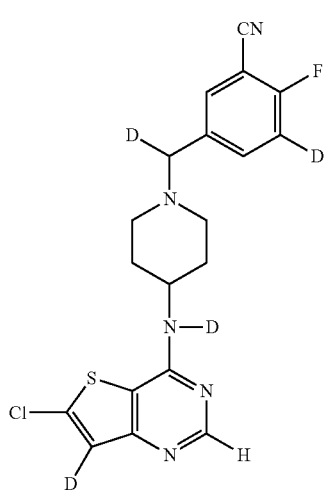
54
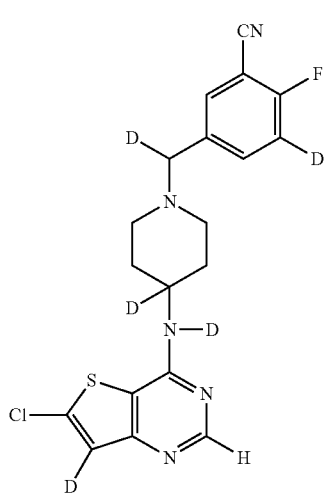

41
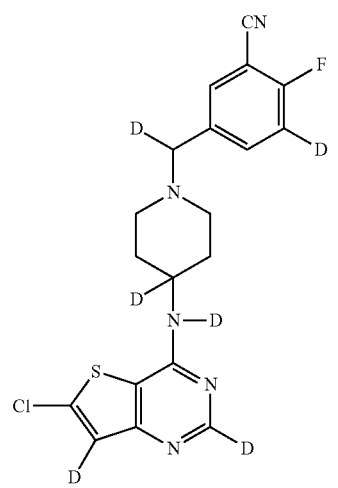
55
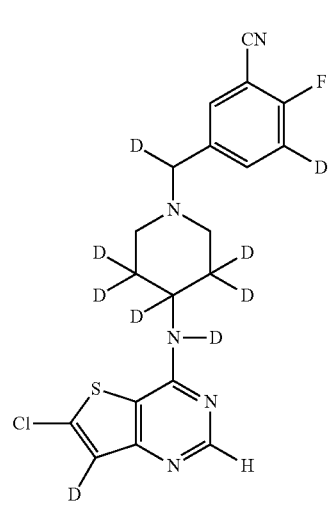
56
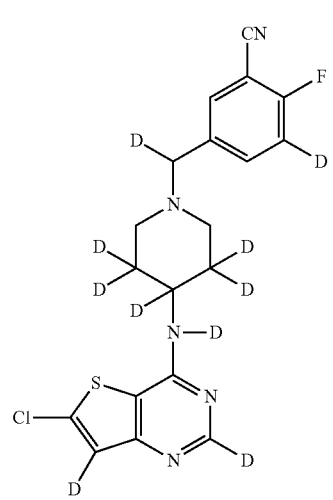
57
42
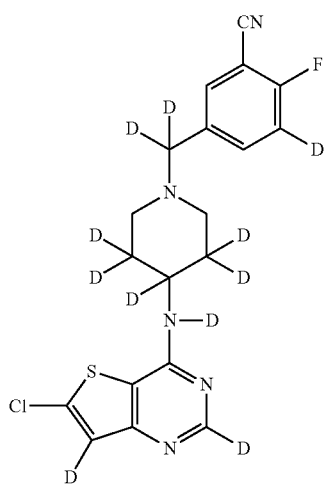
58
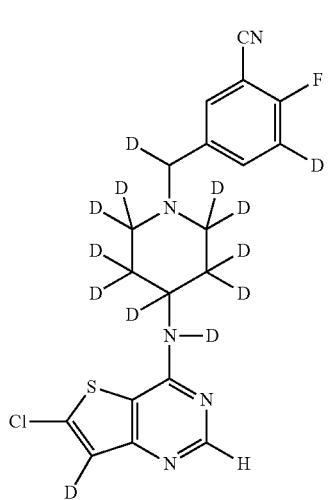
59
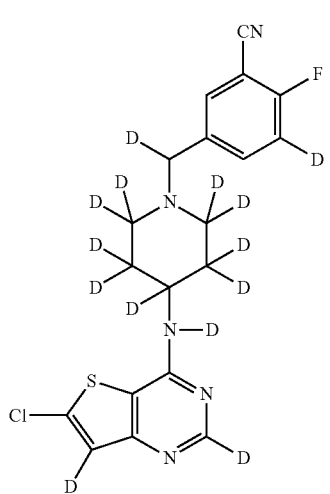
60

43
-continued
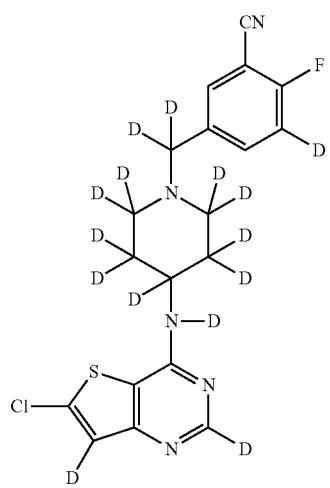
61
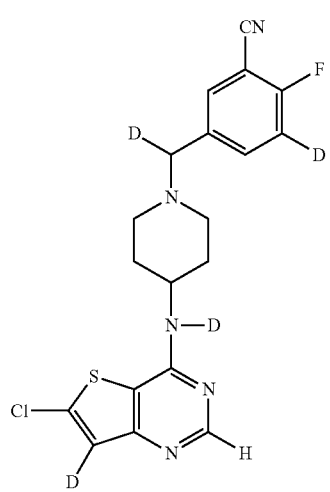
62
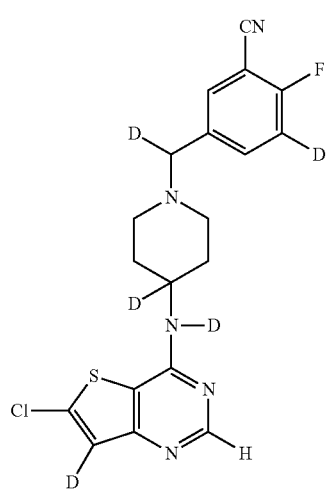
63
44
-continued
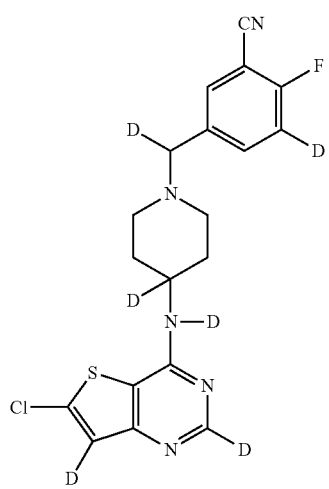
64
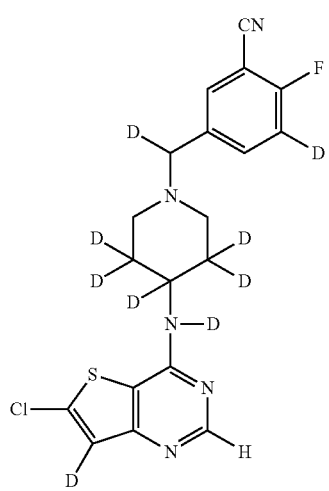
65
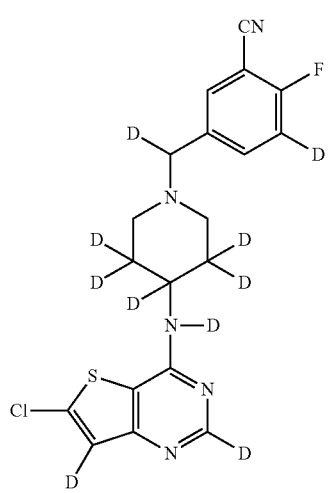
66

-continued
67
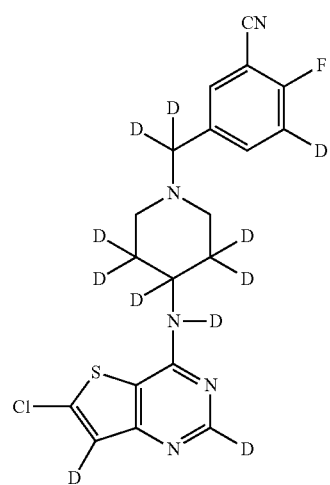
68
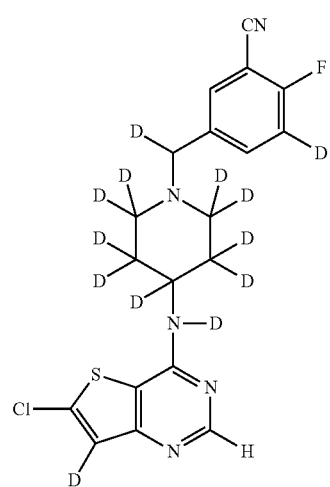
69
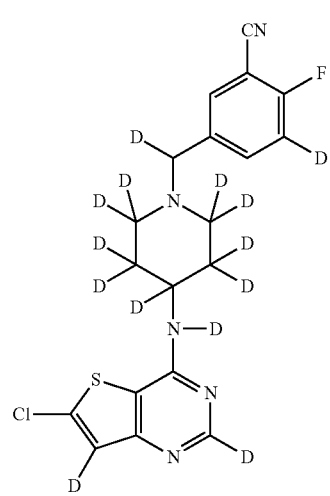
-continued
70
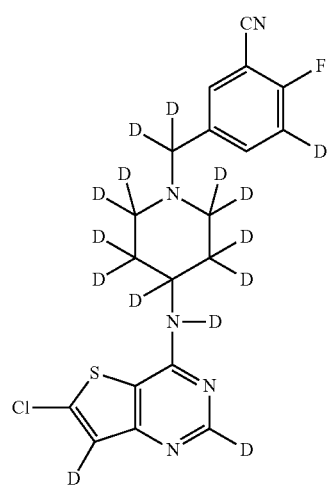
71
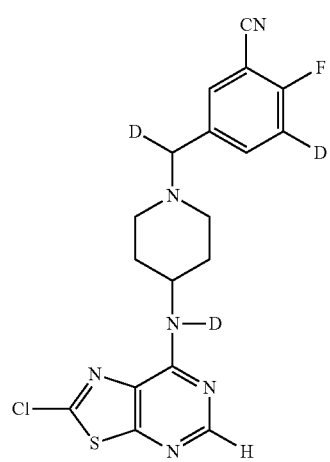
72
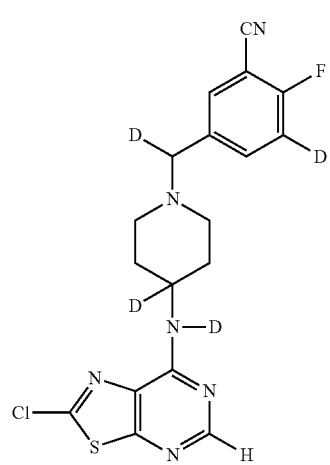

73
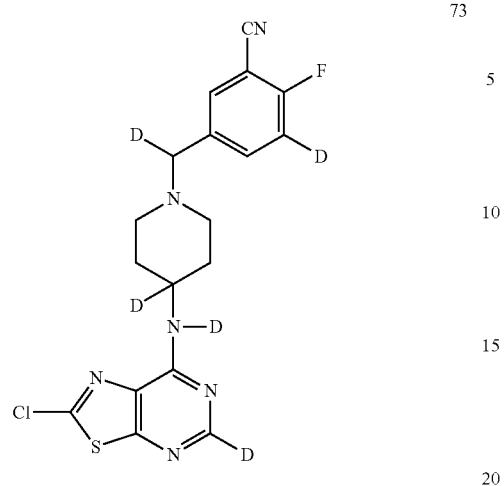
74
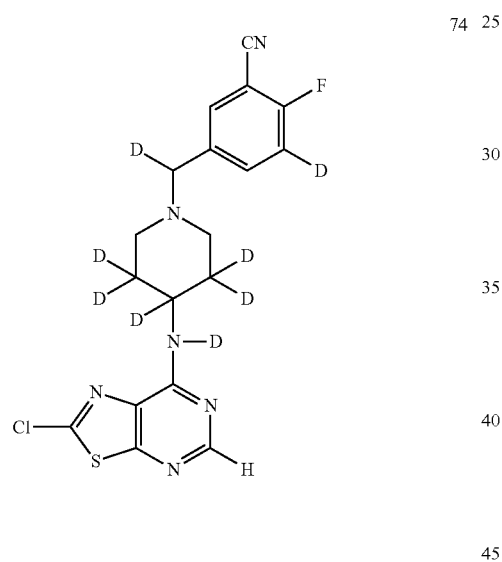
75
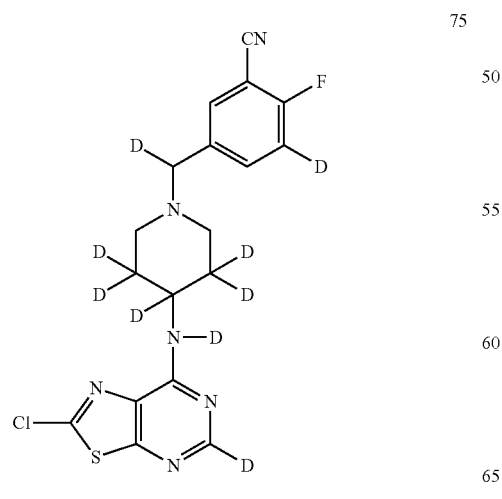
76
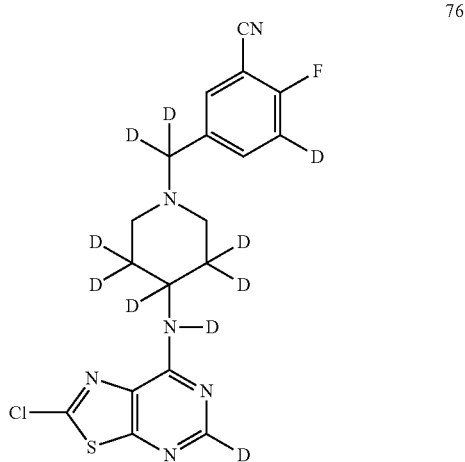
77
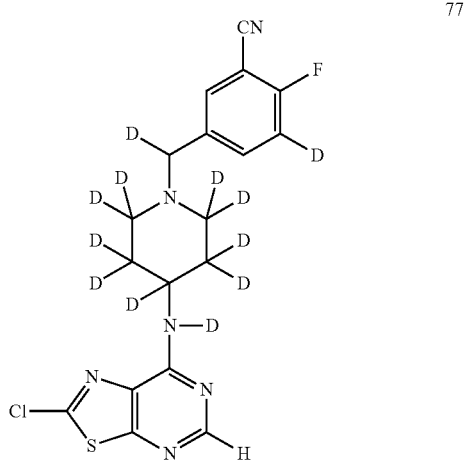
78
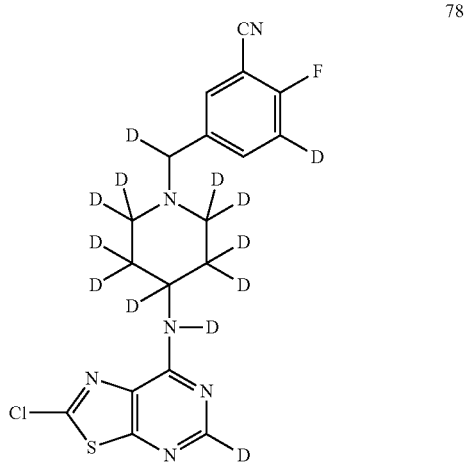

-continued

79

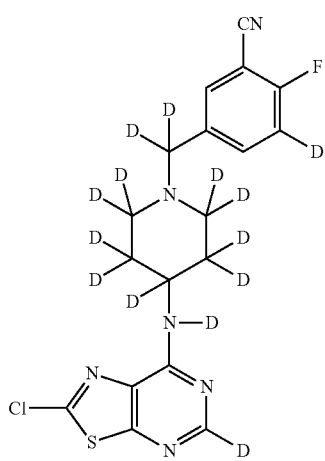

Those skilled in the art will recognize or be able to ascertain using no more than routine experimentation, numerous equivalents to the specific reagents can be utilized to produce compounds of the invention. Numerous modifications and variations of the present invention are possible and therefore it is understood that within the scope of the appended claims, the invention may be practiced otherwise that as specifically described herein. Other aspects, advantages and modifications are within the scope of the invention.

What is claimed is:

1. A deuterium-enriched compound of formula 1,

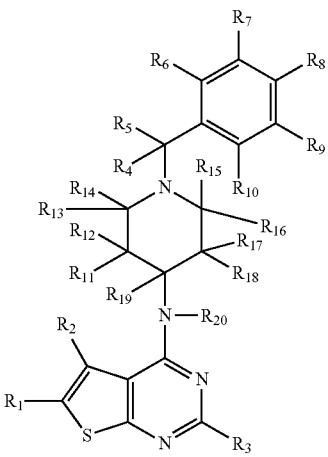

or a pharmaceutically acceptable salt thereof, wherein
$R_1$ is Cl;
$R_2$ is independently selected from H, D, F or Cl;
$R_3$ is independently selected from H or D;
$R_4$ and $R_5$ are independently selected from D or H;
$R_6$, $R_7$, $R_8$, $R_9$ and $R_{10}$ are independently selected from D, H, F, Cl or CN;
$R_{11}$, $R_{12}$, $R_{13}$, $R_{14}$, $R_{15}$, $R_{16}$, $R_{17}$, $R_{18}$, and $R_{19}$ are independently selected from D or H; and
$R_{20}$ is selected from D or H.

2. The deuterium enriched compound of claim 1 wherein the abundance of deuterium is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 755, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%.

3. The deuterium enriched compound of claim 1 wherein,
$R_2$ is D or H;
$R_6$ is H or D;
$R_7$ is CN, F or Cl;
$R_8$ is F, D or H;
$R_9$ is D or H and
$R_{10}$ is D or H.

4. A deuterium enriched compound, or a pharmaceutically acceptable salt thereof, selected from the group consisting of:

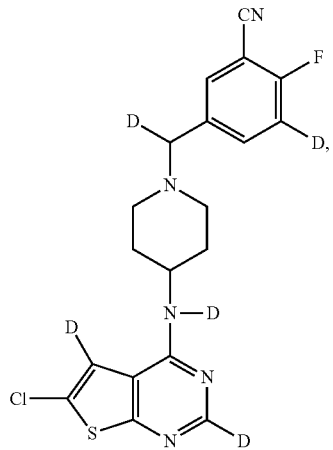

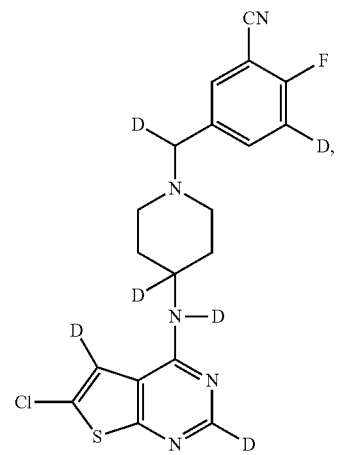

51
-continued
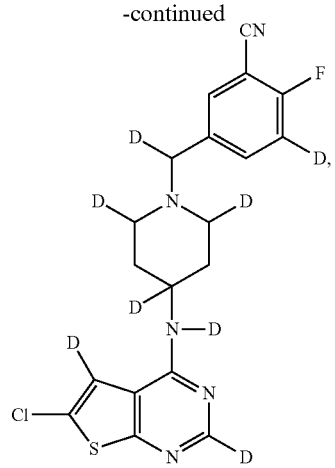
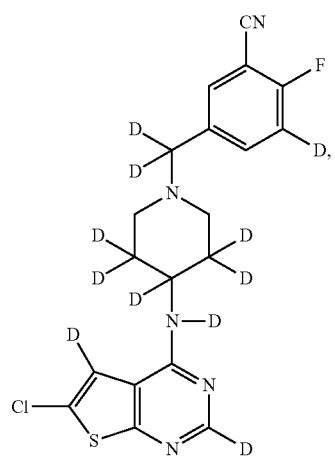
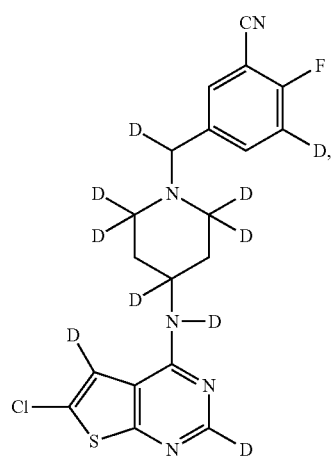
52
-continued
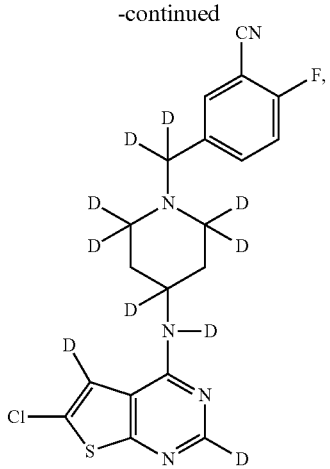
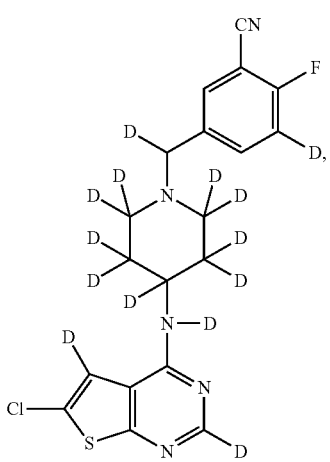
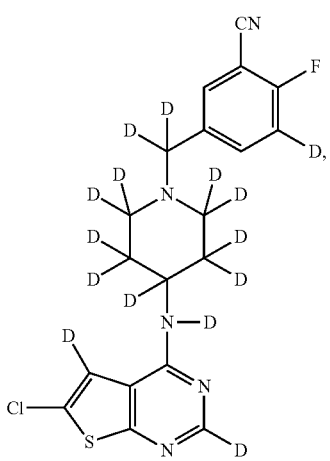

53
-continued
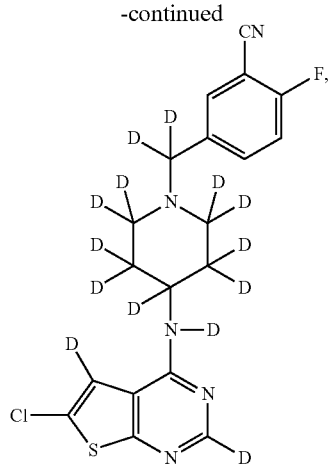
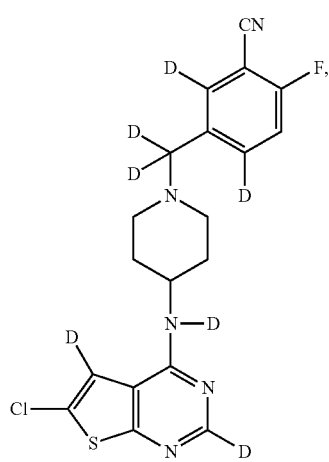
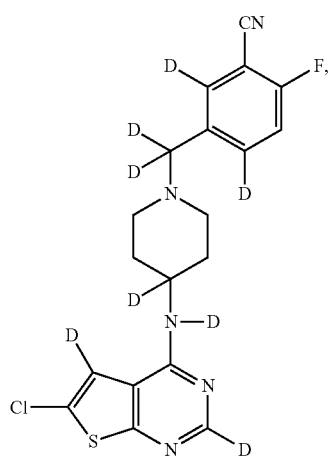
54
-continued
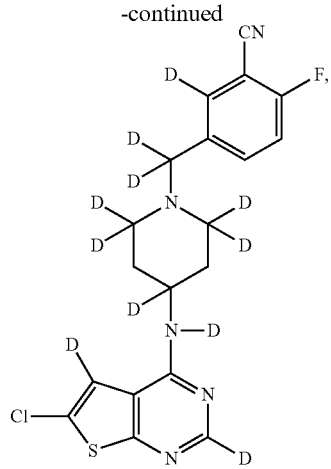
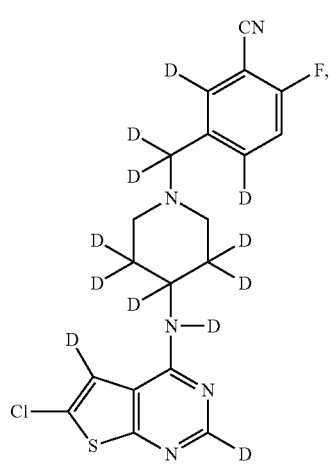
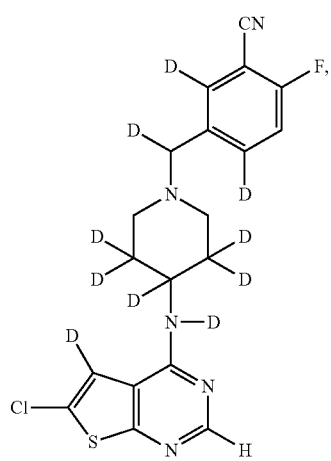

55
-continued
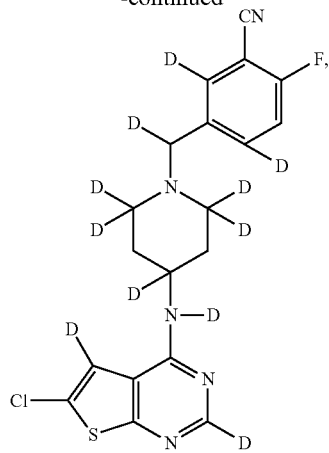
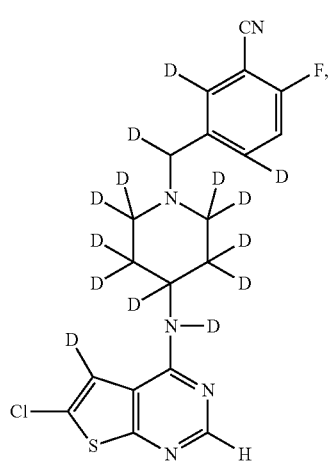
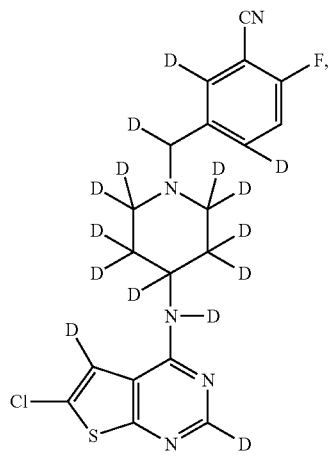
56
-continued
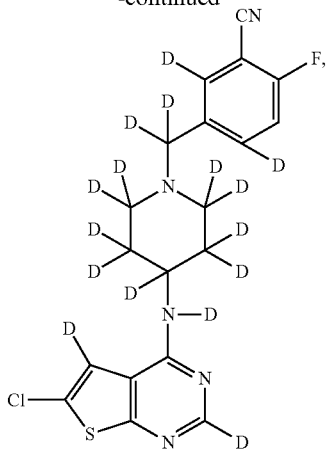
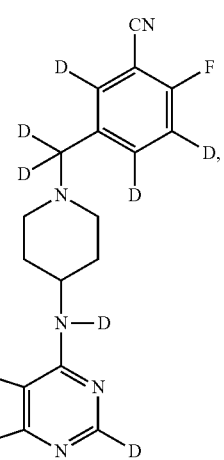
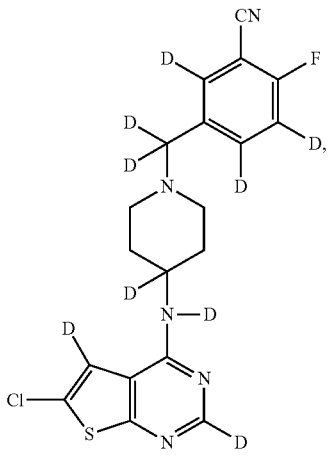

-continued
57
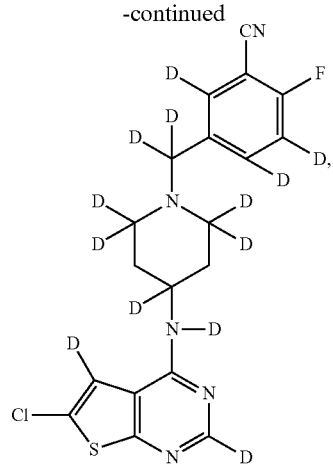
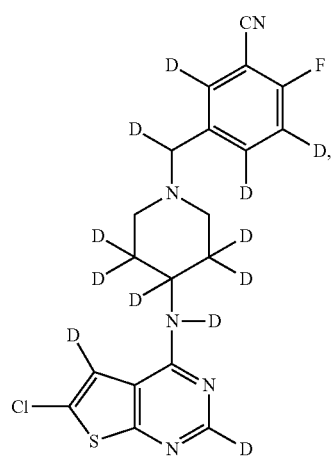
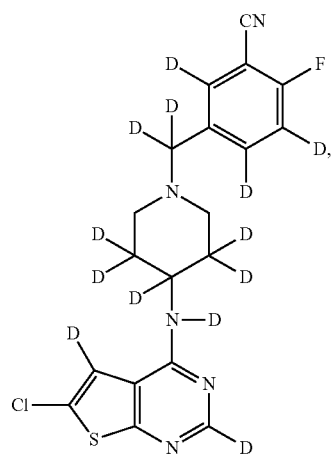
-continued
58
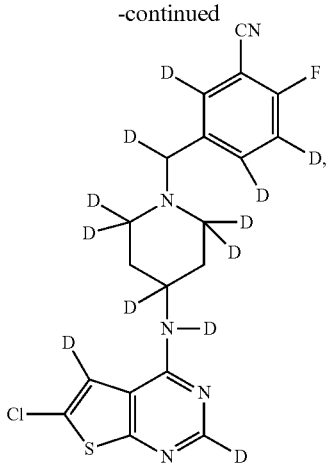
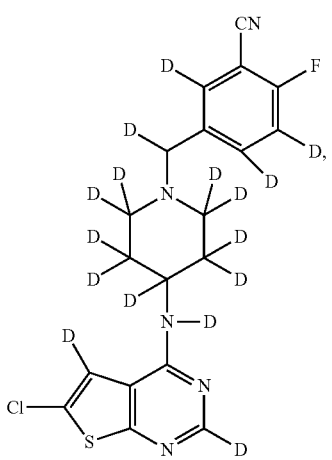
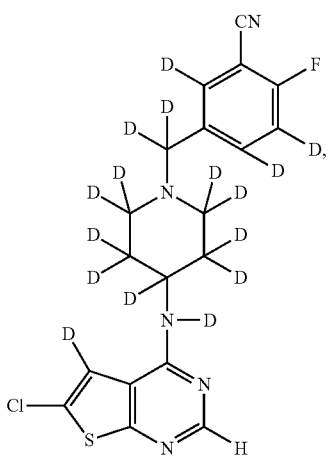

59
-continued
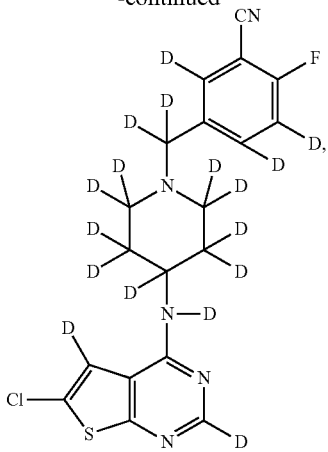
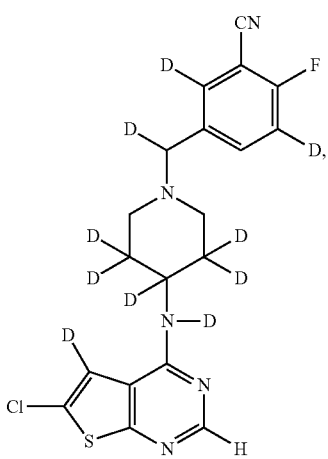
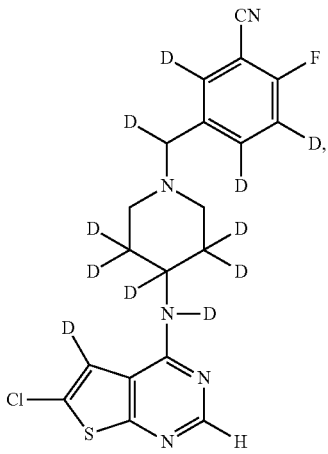
60
-continued
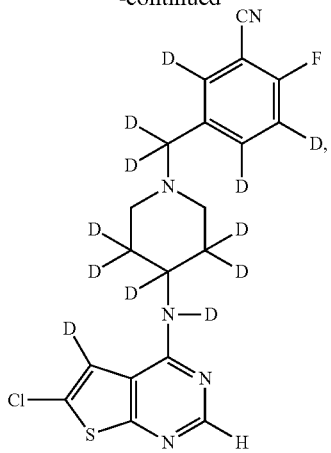
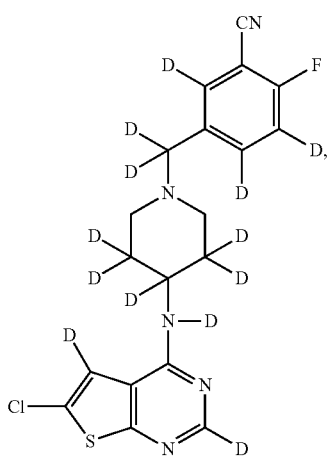
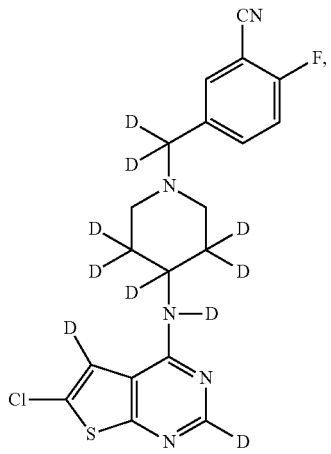

61
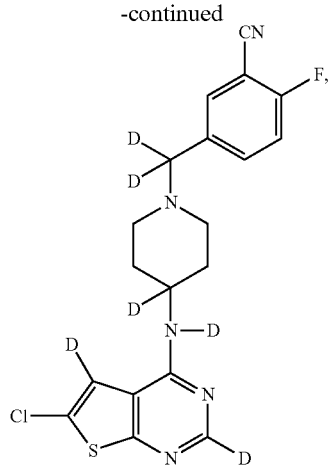
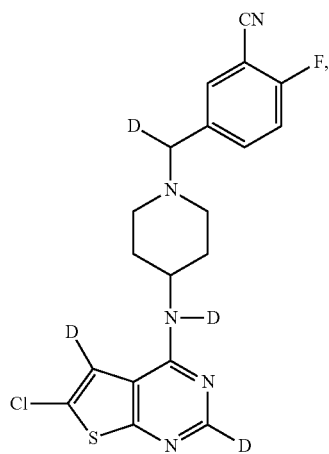
62
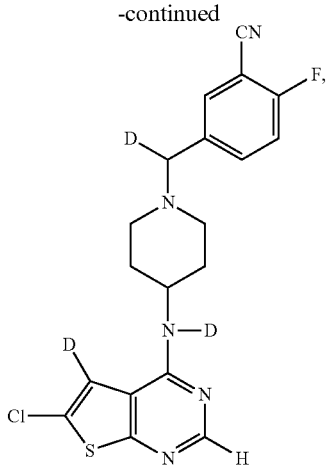
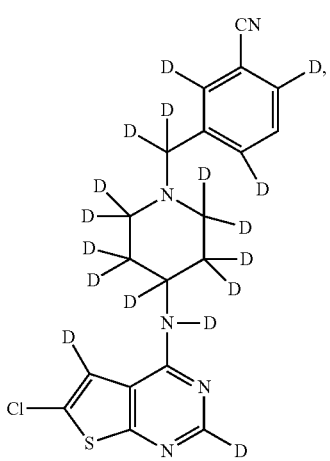
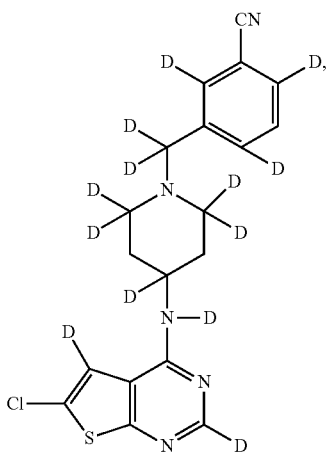

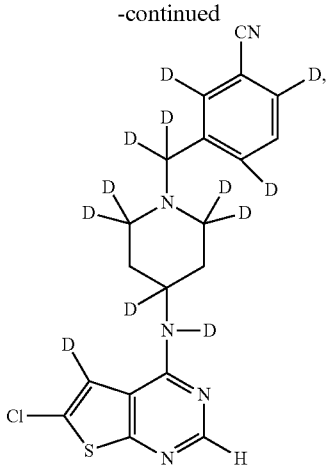
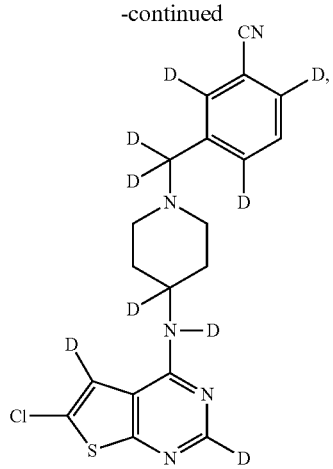
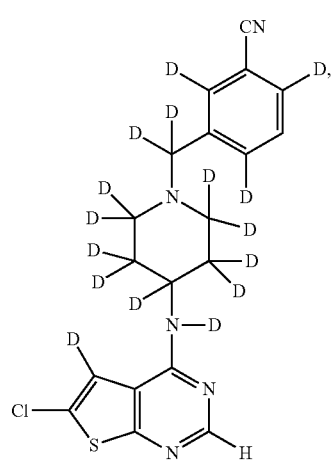
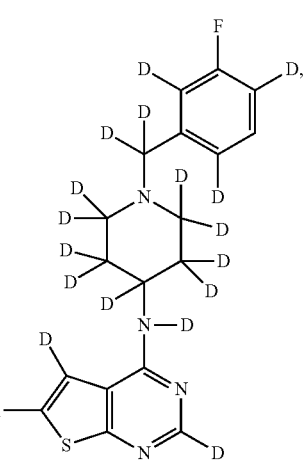
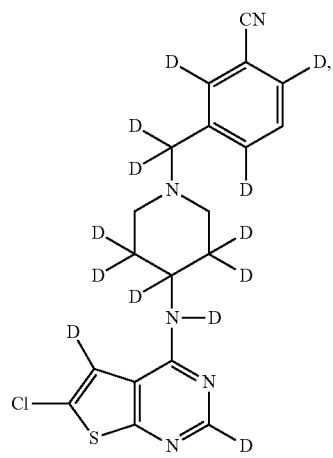
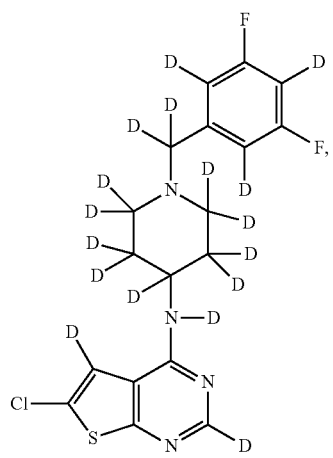

-continued
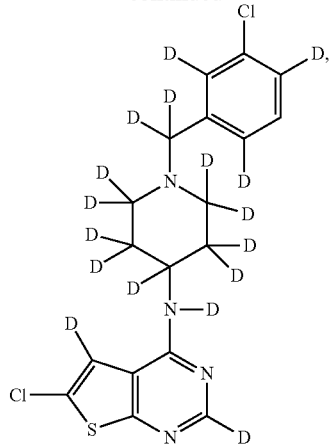
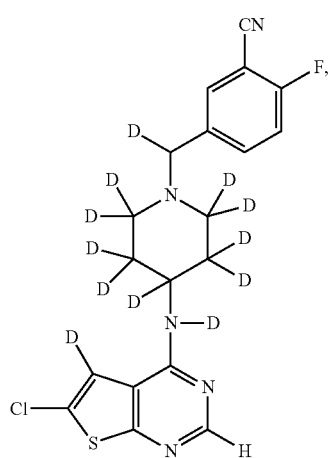
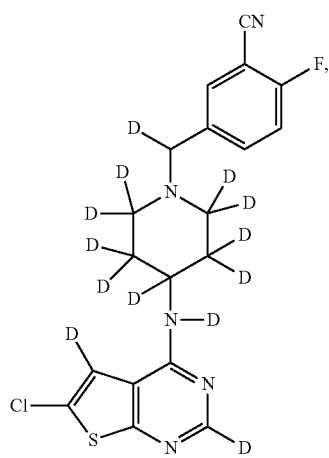
-continued
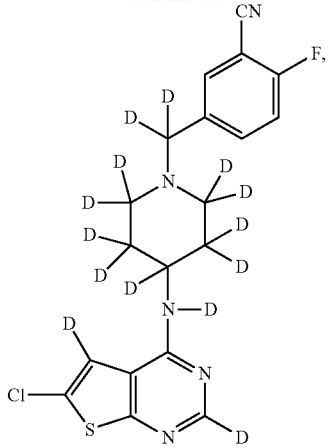
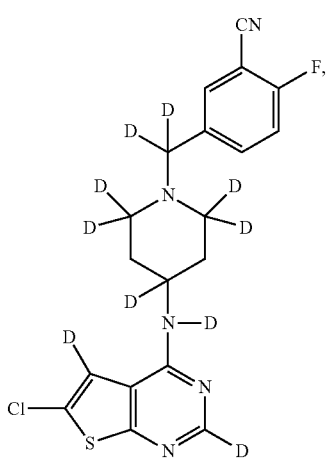
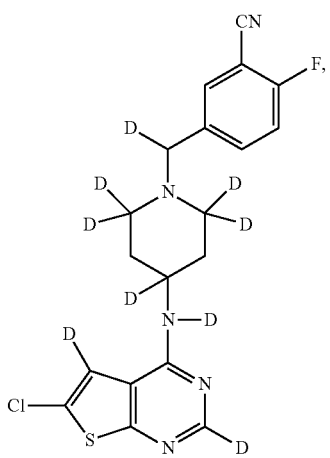

-continued
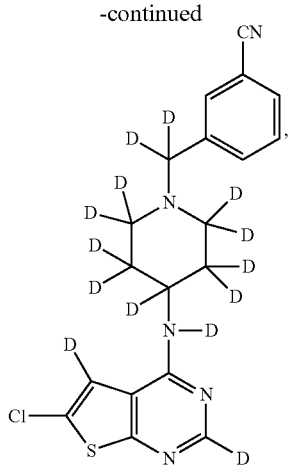
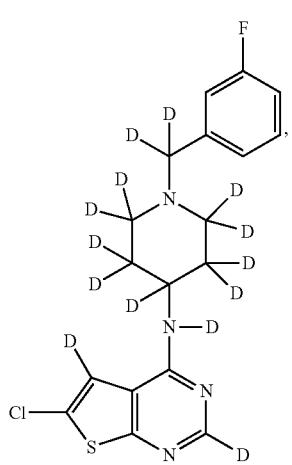
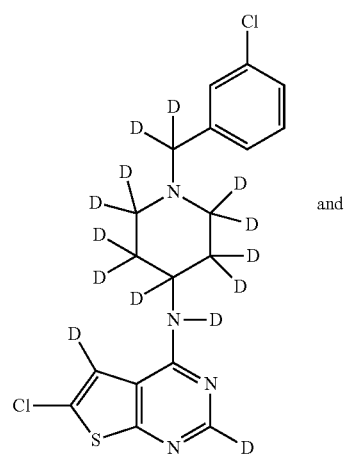
and
-continued
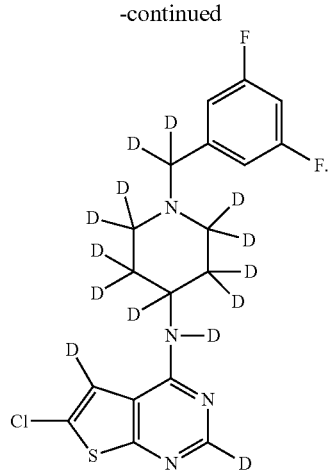
5. The compounds of claim 4, and pharmaceutically acceptable salts thereof, selected from the group consisting of,
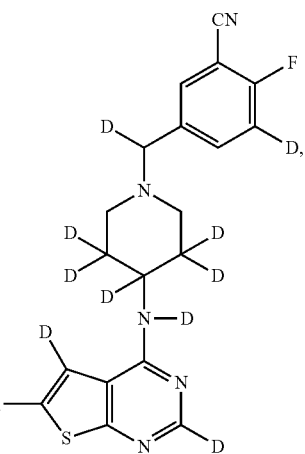
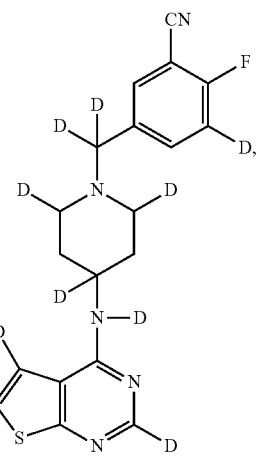

-continued
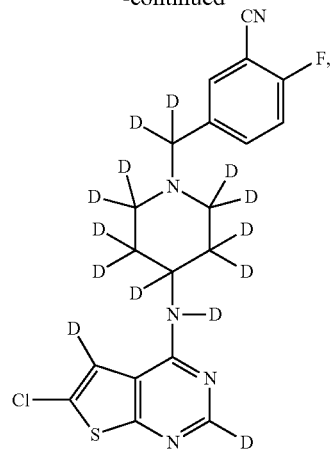
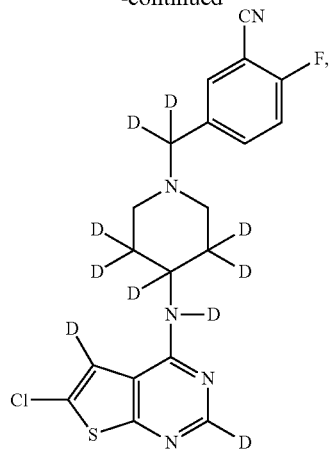
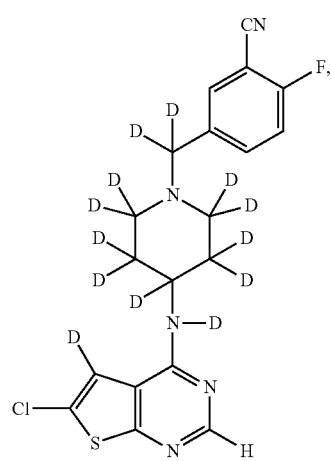
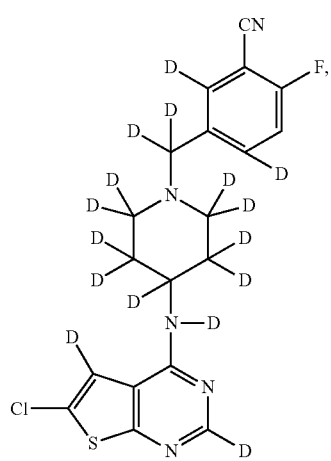
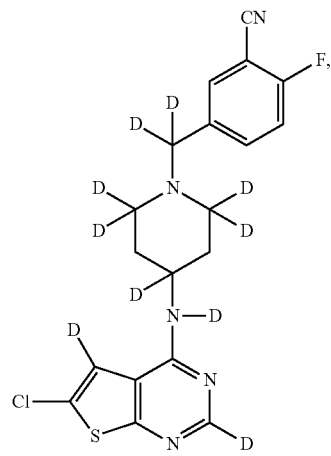
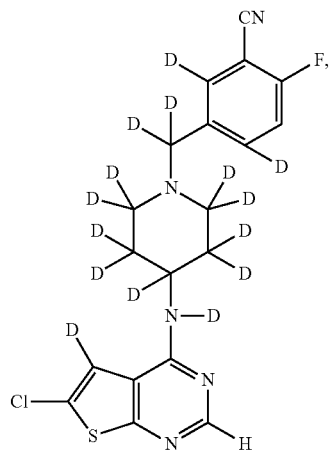

71
-continued
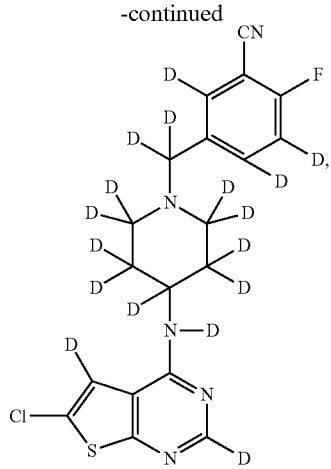
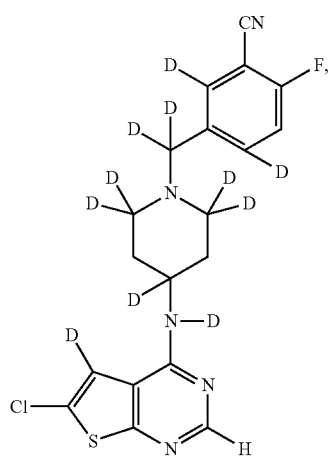
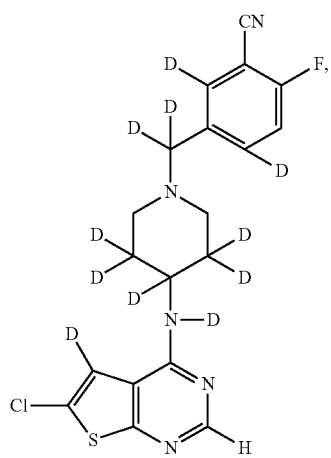
72
-continued
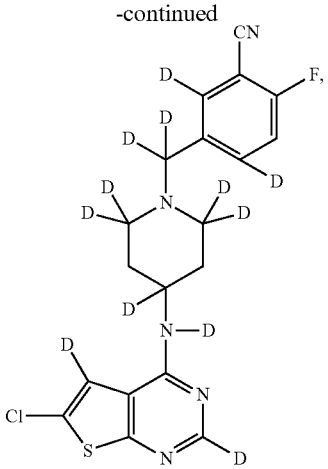
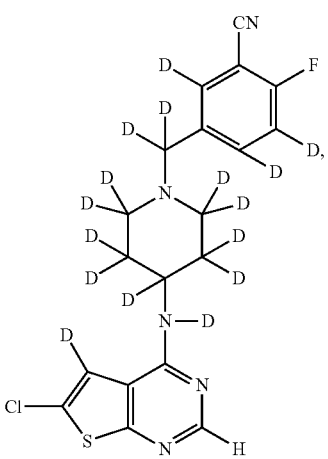
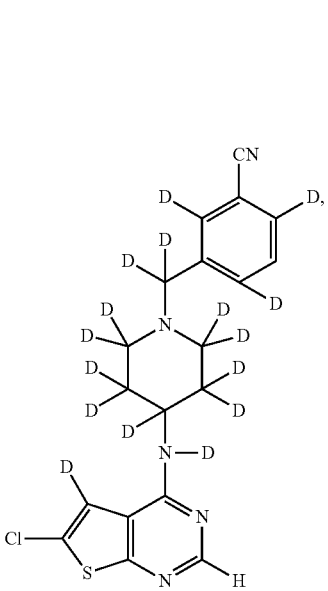

-continued
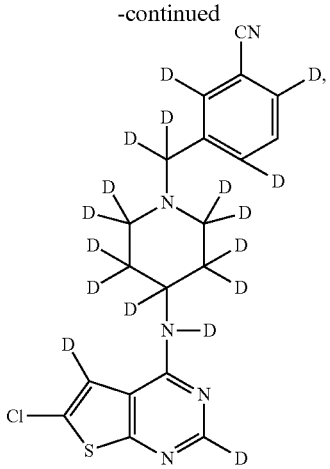
-continued
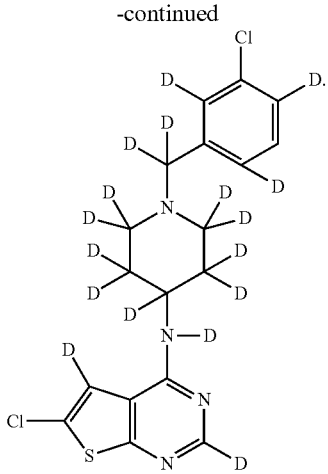
6. The compounds of claim 5, and pharmaceutically acceptable salts thereof, selected from the group consisting of,
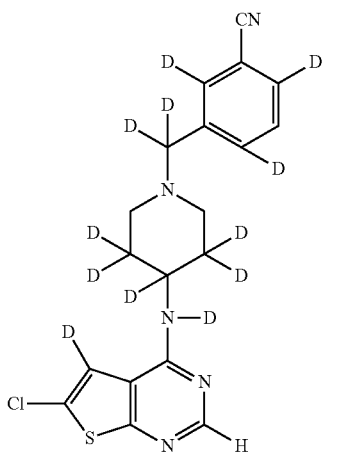

75
-continued
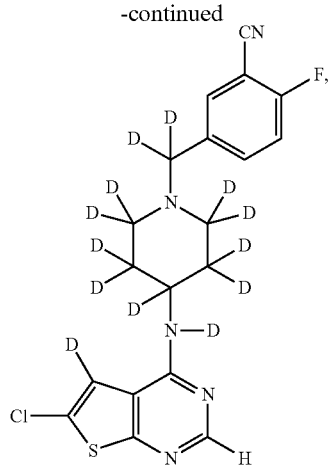
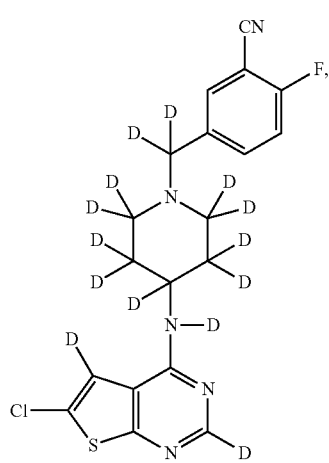
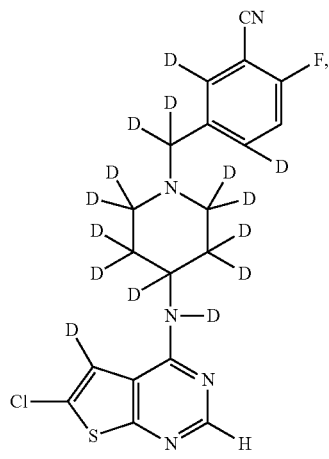
76
-continued
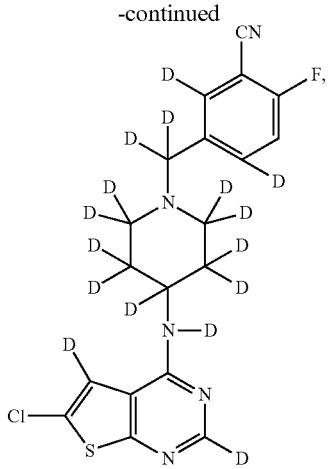
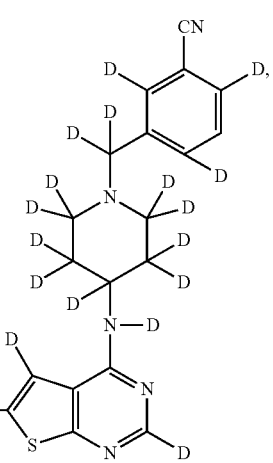
and
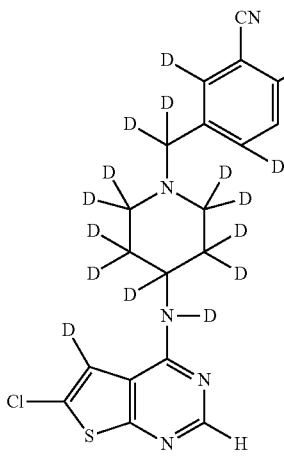

77
-continued
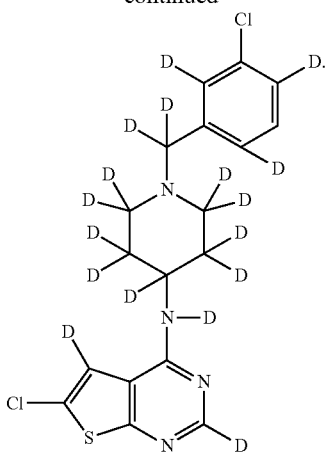
78
-continued
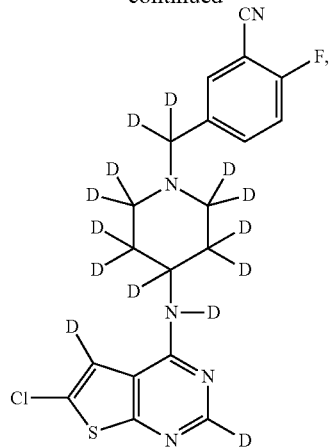
7. The compounds of claim 6, and the pharmaceutically acceptable salts thereof, wherein the compound is selected from the group consisting of
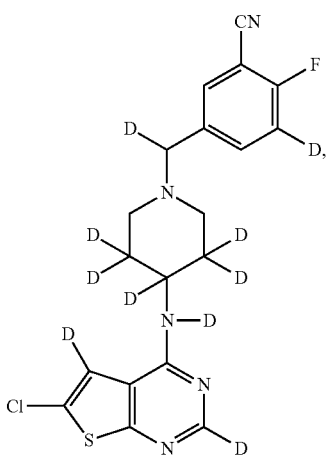
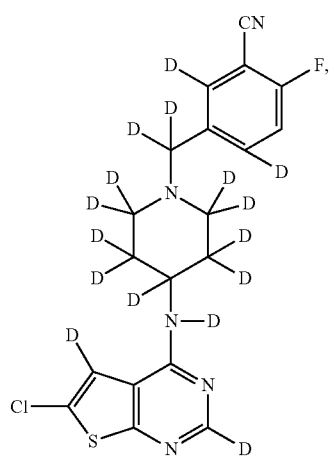
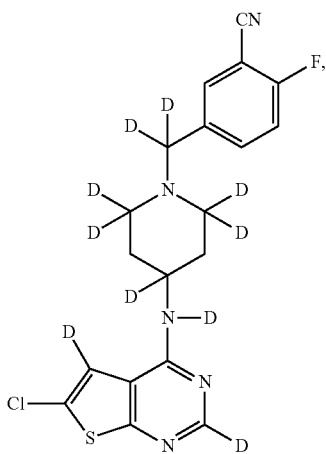
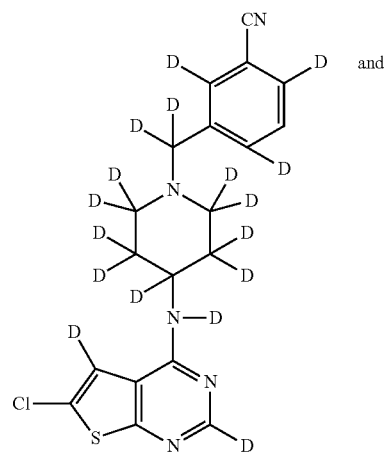
and -continued

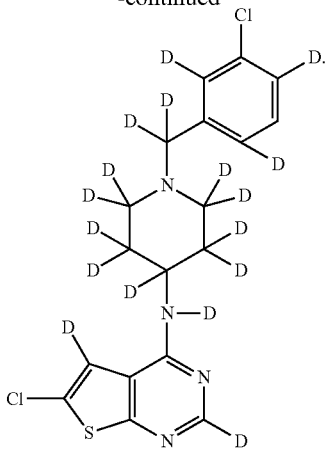

8. The compounds of claim 4 wherein the pharmaceutically acceptable salt is selected from the group consisting of HCl, HBr, maleate, fumarate, acetate, citrate, succinate oxalate, tartarate, lactate, mesylate, and brosylate.

9. The compounds of claim 6 wherein the pharmaceutically acceptable salt is maleate.

10. A method of treating pulmonary arterial hypertension, pulmonary hypertension associated with chronic obstructive pulmonary disease, heart failure, right ventricular hypertrophy, pulmonary vascular remodeling, or asthma, comprising administering to a patient in need of such treatment a pharmaceutically effective amount of a compound of claim 1 or a pharmaceutically acceptable salt thereof.

11. The method of claim 10 wherein a pharmaceutically effective amount or a compound of claim 1, or a pharmaceutically acceptable salt thereof, is used in combination with existing therapies to treat pulmonary arterial hypertension, pulmonary hypertension associated with chronic obstructive pulmonary disease, chronic obstructive pulmonary disease, heart failure, right ventricular hypertrophy, pulmonary vascular remodeling, and asthma.

* * * * *